United States Patent [19]
de Boer et al.

[11] Patent Number: 5,948,889
[45] Date of Patent: Sep. 7, 1999

[54] COMPOSITIONS AND METHODS FOR SCREENING ANTIMICROBIALS

[75] Inventors: Piet A. J. de Boer; Cynthia A. Hale, both of University Heights, Ohio

[73] Assignee: Case Western Reserve University, Cleveland, Ohio

[21] Appl. No.: 08/651,818

[22] Filed: May 21, 1996

[51] Int. Cl.$^6$ ................ C07K 14/195; C07K 14/245; C07K 17/02; C07K 17/14
[52] U.S. Cl. .................. 530/350; 530/810; 530/811; 530/814; 530/817; 530/825; 930/200; 930/280
[58] Field of Search .................. 530/350, 810, 530/811, 814, 817, 825; 930/200, 280

[56] References Cited

U.S. PATENT DOCUMENTS

| | | | |
|---|---|---|---|
| 4,016,043 | 4/1977 | Schuurs et al. | 435/5 |
| 4,018,653 | 4/1977 | Mennen | 600/572 |
| 4,424,279 | 1/1984 | Bohn et al. | 436/534 |
| 4,568,649 | 2/1986 | Bertoglio-Matte | 436/534 |
| 4,683,195 | 7/1987 | Mullis et al. | 435/6 |
| 4,683,202 | 7/1987 | Mullis | 435/91.2 |
| 5,310,663 | 5/1994 | Dobeli et al. | 435/69.7 |

OTHER PUBLICATIONS

W.K. Joklik et al., [eds.], *Zinsser Microbiology*, 18th ed., Appleton–Century–Crofts, Norwalk, CT, (1984), p. 193.
*Jawetz, Melnick & Adelberg's Medical Microbiology*, 19th ed, Appleton & Lange, Norwalk, CT (1991), p. 150.
J.F. Sessegolo et al., "Distribution of Serotypes and Antimicrobial Resistance of *Streptococcus pneumoniae* Strains Isolated in Brazil From 1988 to 1992", J. Clin. Microbiol., 32:906–911 (1994).
Anderson and Young, Quantitative Filter Hybridization in *Nucleic Acid Hybridization* (1985) pp. 73–111.
G.F. Brooks et al., *Jawetz, Melnick & Adelberg's Medical Mirobiology*, 19th ed, Appleton & Lange, Norwalk, CT (1991), p. 155.
Douillard and Hoffman, Basic Facts about Hybridomas, in *Compendium of Immunology*, vol. II, ed. by Schwartz (1981).
Kohler and Milstein, Nature 256:495–499 (1975).
European Journal of Immunology 6:511–519 (1976).
Reading, Journal of Immunological Methods 53:261–291 (1982).
Sambrook et al., *Molecular Cloning, A Laboratory Manual*, 2nd Ed., (Cold Spring Harbor Press, NY (1989).
M.A. Blanar and W.J. Rutter, "Interaction Cloning: Identification of a helix–loop–helix Zipper Protein that Interacts with cFos," Science 256:1014 (1992).
P.A.J. de Boer et al., "Isolation and Properties of minB, a Complex Genetic Locus Involved in Correct Placement of the Division Site in *Escherichia coli* " *Journal of Bacteriology*, 170:2106 (1988).
Ausubel et al., *Current Protocols in Molecular Biology* (John Wiley & Sons) (pp. 13.14.1–13.14.14) (1994).

A Higashitani et al., "A Cell Division SulA of *Escherichia coli* Directly Interacts with FTSZ Through GTP Hydrolysis," Biochemical and Biophysical Research Communications, 209: 198–204 (1995).
W. Margolin et al., "Cloning and Characterization of a *Rhizobium meliloti* Homolog of the *Escherichia coli* Cell Division Gene ftsZ," Journal of Bacteriology 173(18): 5822–5830 (1991).
A. Nishimura, "The new gene controlling the frequency of cell division per round of DNA replication in *Escherichia coli*," Molecular and General Genetics 215:286–293 (1989).
B. Beall et al., "Cloning and characterization of *bacillus subtilis* homologs of *Escherichia coli* cell division genes ftsZ and ftsA," Journal of Bacteriology 170: 4855–4864 (1988).
J. Ward et al., "A lac–ftsZ gene fusion is an analog of cell division inhibitor sulA," Journal of Bacteriology 157:815–820 (1984).
E. Bi et al., "Cell division Inibitors SulA and MinCD prevent formation of the FtsZ ring," Journal of Bacteriology 175:1118–1125 (1993).
E. Harry et al., "Cloning and expression of a *Bacillus subtilis* division initiation gene for which a homolog has not been identified in another organism," Journal of Bacteriology 171:6835–6839 (1989).
W. Margolin et al., "*Rhizobium meliloti* contains a novel second homolog of the cell division gene ftsZ," Journal of Bacteriology 176:2033–2043 (1994).
K. Cam et al., "Sigma S–dependent overexpression of ftsZ in *Escherichia coli* K–12 rpoB mutant that is resistant to the division inhibitors DicB and DicF RNA," Molecular and General Genetics 248:190–194 (1995).
I. Ruberti et al., "A class of gyrB mutants, substantially unaffected in DNA topology, suppressed the *Escherichia coli* K12 fts$Z_{84}$ mutation," Molecular Microbiology 5(5): 1065–1072 (1991).
D. Vinella et al., "Penicillin–Binding Protein 2 Inactivation in *Escherichia coli* Results in Cell Division Inhibition, Which is Relieved by FtsZ Overexpression," Journal of Bacteriology 175:6704–6710 (1993).
Y. Ishino et al., "Nucleotide sequence of the lig gene and primary structure of DNA ligase of *Escherichia coli*," Molecular and General Genetics 204:1–7 (1986).
C. Byrne et al., "DNA sequences of the cysK regions of *Salmonella typhimurium* and *Escherichia coli* and linkage of the cysK regions to ptsH," Journal of Bacteriology 170: 3150–3157 (1988).

(List continued on next page.)

*Primary Examiner*—Dian C. Jacobson
*Attorney, Agent, or Firm*—Medlen & Carroll, LLP

[57] ABSTRACT

A method for screening compounds for antimicrobial activity is described that utilizes bacterial protein-protein binding in vitro. The method may be performed using immobilized elements and the immobilization may be carried out using a variety of immobilization means (e.g., columns, beads, adsorbents, nitrocellulose paper, etc.) in order to screen large libraries of compounds.

10 Claims, 13 Drawing Sheets

OTHER PUBLICATIONS

R. Fleisschmann et al., "Whole–genome random sequencing and assembly of *Haemophilus influenzae* Rd," *Science* 269:496–512 (1995).

P.R. Murray et al., "Antimicorbial Susceptibility Testing: General Considerations," *Manual of Clinial Microbiology,* ASM Press, Washington, D.C., pp. 1277–1280 (1995).

Morch, M.–D. *Nucleic Acids Research* 16:6157–6172 (1988).

Meador, J. III et al. *Gene* 95:1–7 (1990).

Chang–Yeh, A. et al. *Nucleic Acids Research* 19(13):3667–3672 (1991).

| FIG. 4A | FIG. 4B |
|---|---|
| FIG. 4C | FIG. 4D |
| FIG. 4E | FIG. 4F |

```
  1  CAATACCAGGGATGAAGTAAAGAATTAGTAATACAATTGCGCGGGCAGATACCAGGCAAA
     G  I  G  P  I  F  Y  L  I  L  L  V  I  A  R  P  L  Y  W  A  F

121  TATCTGGGCGGTGTAGCGCCAGTCAATCGTGCTTCCAGTTGTTCAGCCAATAAACCGTTAAA
     T  D  P  P  T  A  G  T  L  R  A  E  L  Q  E  A  L  L  G  N  F

241  AGATGACACGCAGAGGCCACAACAGATAACTCAGCCATTGTAGCCAGTCCGGAACGTAACT
     S  I  V  R  L  P  W  L  L  Y  S  L  W  N  D  P  V  Y  S

361  TCAACAAAATATTGACCAGAGCCGGTAAAAATAACGAAACGCCGAATCCCAGGTTGCGAGAC
     M  L  I  N  V  L  L  P  L  I  V  F  R  R  I  G  P  Q  S  V

481  AAACCATAATCAGGATGAGCTCCTTTTGACCAATCCCAGGAAAATTCTGGTATTTTACCG
     S  V  M
     <-- cysZ Bgl 601  ATCTATCTTTGTGCTGTGAAAGTTAATAGTGCACTTGAGGTAATCGGCAAATACT
                                               Pvul 721  TGCAGGATTTGCGTCTGATATTAATCATTGTTGGCGCGATCGCCATAATCGCTTTACTGGT
     Q  D  L  R  L  I  L  I  I  V  G  A  I  A  I  I  A  L  L  V
```

```
TTTTTGCCATTCGCGTTTCATGATTCCGCGGCACATCTTTCATGATACCGAAAATCCCGG
 K  Q  W  E  R  K  M  I  R  P  V  D  K  M  I  G  F  I  G

CGGAGCGGGCAATCCAGTTAGCAATCGTGGAGAAGAAATAGCCAAACACTAACAGCACAG
 P  A  A  I  W  N  A  I  T  S  F  F  Y  G  F  V  L  L  V
                  BamHI
                    |
CATGAGAGTCGGGGATCCAGACATCGAGCTGTGTAAAGAGCCACCAGAATGCGCCCCCA
 M  L  T  P  I  W  V  D  L  Q  T  F  L  W  F  A  G  G

GAGCTTCCAGCCCTTGCGCAAAATAGTAAAAACCGCTGCGTGGGCAGATGTGAATGATG
 L  K  W  G  Q  A  F  Y  Y  F  G  S  R  P  A  S  T  F  S

GGTAATTGCGCAATGGACAGTTAGGATATGTTCGAAAAAACAGCAAAAGCACGATTTC

CTTAGTGAGTAAATGTTTGCCGTGGTGGCAAGGTGTTAGAACAACAGAGAATATAATGA
                                                     M  M
                                        ~~~      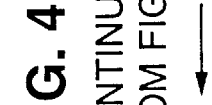
                                        PvuI  zipA -->
                                         |
ACATGGTTTCTGGACCAGCCGTAAAGAACGATCTTCTATGTTCCGCGATCGGCCATTAA
 H  G  F  W  T  S  R  K  E  R  S  S  M  F  R  D  R  P  L  K
```

FIG. 4B
CONTINUED
FROM FIG. 4A

CONTINUED
ON FIG. 4D

FIG. 4C
FROM FIG. 4A
CONTINUED ON FIG. 4D
CONTINUED ON FIG. 4E

```
841   AACGAATGAAGTCAAAAACGTGACGACGATTCTTATGACGAGGATGTCGAAGATGATGAGG
       R  M  K  S  K  R  D  D  D  S  Y  D  E  D  V  E  D  D  E  G

961   AGGCTGCTCGTCCGTCGCCCGCAACACCAGTACCAACCGCCCTTATGCGTCTGCGCAGCCGCG
       A  A  R  P  S  P  Q  H  Q  Y  Q  P  P  Y  A  S  A  Q  P  R

1081  CGCAGCCGGTGCAGCAGCCTGCCTATCAGCCGCAGCCTGAACAGCCGTTGCAGCAGCCAGT
       Q  P  V  Q  Q  P  A  Y  Q  P  Q  P  E  Q  P  L  Q  Q  P  V
                                                PstI

1201  AGGCTTTCCAGCCTGCAGAACCCGTAGCGGCACCACAGCCTGAGCCTGTAGGGAACCTGC
       A  F  Q  P  P  A  E  P  V  A  A  P  Q  P  E  P  V  A  E  P  A
         BglI

1321  ATCACGGTAGCGAGCTAAACGGTGAAGCTCTTCTTAACAGCATTCAACAAGCGGGCTTCAT
       H  G  S  E  L  N  G  E  A  L  L  N  S  I  Q  Q  A  G  F  I
         KpnI PstI

1441  TATTCAGCCTGGCGAATATGGTGAAACCGGGAACCTTTGATCCTGAAATGAAGGATTTCAC
       F  S  L  A  N  M  V  K  P  G  T  F  D  P  E  M  K  D  F  T

1561  TCAAGCTGATGCTGCAATCTGCCGCAGCATATTGCCGATGAAGTGGGCGGTGTCGTGCTTGA
```

```
CGTTGGTGAGGTTCGTGTTCACCGCGTGAATCATGCCCCGGCTAACGCTCAGGAGCATG
 V  G  E  V  R  V  H  R  V  N  H  A  P  A  N  A  Q  E  H  E
         AgeI KpnI
TCAACCGGTCCAGCAGCCGCCTGAAGGCCAGGCAGGTACCGCCGCAACATGTTCCGCATCCAG
 Q  P  V  Q  Q  P  P  E  A  Q  V  P  P  Q  H  A  P  H  P  A

TTCGCCACAGGTCGGCGGCCAGCGCCGCCAGCCTGTGCATTCAGCACCGGCAACCGGCACAAC
 S  P  Q  V  A  P  A  P  Q  P  V  H  S  A  P  Q  P  A  Q  Q

TCCAGTTATGGATAAAACCGAAGCGCAAAGAAGGCGGTGATTATCATGAACGTCGCGGCGC
 P  V  M  D  K  P  K  R  K  E  A  V  I  I  M  N  V  A  A  H

TTTTGGCGATATGAATATTTACCATCGTCATCTTAGCCCGGATGGCAGCGGCCCGGGCGT
 F  G  D  M  N  I  Y  H  R  H  L  S  P  D  G  S  G  P  A  L

TACTCCGGGTGTCACTATCTTTATGCAGGTACCGTCTTACGGTGACGAGCTGCAGAACT
 T  P  G  V  T  I  F  M  Q  V  P  S  Y  G  D  E  L  Q  N  F

CGATCAGCGCCGTATGATGACTCCGCAGAAATTGCGCGAGTACCAGGACATCATCCGCG
```

FROM
FIG. 4B

FIG. 4D
CONTINUED
FROM FIG. 4C

CONTINUED
ON FIG. 4F

FIG. 4E
FROM FIG. 4C
CONTINUED ON FIG. 4F

```
            K   L   M   L   Q   S   A   Q   H   I   A   D   E   V   G   G   V   V   L   D
1681   AAGTCAAAGACGCCAACGCCCTGATACACTTAAGGCAAATTAACTCCTCTTCGAACCCCGC
            V   K   D   A   N   A   *                   ------>
                                        AflII
1801   GAACTGCGAACGACGCTTCGCCATCATGAATATCTTTATCATGTGATGGATGCGCCGAAA
        E   L   R   T   T   L   R   H   H   E   Y   L   Y   H   V   M   D   A   P   E   I
        HindIII
1921   CCAGAACTGATTACGCCCTGATTCGCCTACTCAACGTGTAGGCGCTGCGCCGCTGGCGGCTT
        P   E   L   I   T   P   D   S   P   T   Q   R   V   G   A   A   P   L   A   A   F
2041   AGCTTTCTTGCTTTCAACAAACGTGTGCAGGACCGTCTGAAAAACAACGAGAAAGTCACCT
        S   F   L   A   F   N   K   R   V   Q   D   R   L   K   N   N   E   K   V   T   W
```

```
D  Q  R  R  M  M  T  P  Q  K  L  R  E  Y  Q  D  I  I  R  E
TTGTCGGGGTTTTTAGCATTGATGGTGCGATATGGAATCAATCGAACAACAACTGACA
         <-------                  M  E  S  I  E  Q  Q  L  T
                                       lig -->

TTCCCGACGCTGAATACGACAGGCTGATGCGCGAACTGCGCGAGCTGGAAACCAAACAT
 P  D  A  E  Y  D  R  L  M  R  E  L  R  E  L  E  T  K  H

TCAGCCAGATACGCCATGAAGTACCAATGCTGTCACTGGATAACGTTTTTGATGAAGAA
 S  Q  I  R  H  E  V  P  M  L  S  L  D  N  V  F  D  R  E

GGTGCTGTGAGCTGAAGCTGGATGGTCTTGCCGTCAGTATTCTGTATGAAAATGGCGTT
 C  C  E  L  K  L  D  G  L  A  V  S  I  L  Y  E  N  G  V
```

FIG. 4F

FROM FIG. 4D

CONTINUED FROM FIG. 4E

FIG. 5

```
  4 DLRLILIIVGAIAIIALLVHGFWTSRKERSSMF.RDRPLKRMKSKRDDDS  52
    ||.|||.||.|:||:|||:||.|.:::.||
  2 DLNTILIIVGIVALVALIVHGLWSNRREKSKYFDKANKFDRTSLTSRSHT  51

53 YDEDVEDDEGVGEVRVHRVNHAPANAQEKEAARPSPQHQYQPPYASAQPR 102
    |::                     |:
 52 QEEMVQPNNISPNTYVENGHTPIPQPTTEKLPSEAELIDYRQSDKSVD..  99

103 QPVQQPPEAQVPPQHAPHPAQPVQ..QPAYQPQPEQPLQQPVSPQVAPAP 150
    :||:|||  |.|     |.|:|   ||:|
100 DIKISIPNTQPIYDMGNHRSEPIQPTQPQYDMPTANNVASMTLEQLEAQS 149

151 QPV......HSAPQPAQQAFQPAEPVAAPQPEPVAEP.APVMDKPKRKE  192
    |.|      |.|                    ||
150 QNVGFNGINSSSPELRVQLAELSHEEHQVDYNLSFNEPKAETTAHPKQTT 199

193 AVIIMNVAAHHGSELNGEALLNSIQQAGFIFGDMNIYHRHLSPDGSGPAL 242
    |:|:    |:|||:||  :::|:||||:|:::
200 GYIQLYLIPKSSEEFNGAKLVQALENLGFILGKDEMYHRHLDLSVASPVL 249

243 FSLANMVKPGTFDP.EMKDFTTPGVTIFMQVPSYGDELQNFKLMLQSAQH 291
    ||:||| |||||| |||||  |::||||:||:|:
250 FSVANLEQPGTFNAYNLAEFNTIGIVLFMQLPSPGNNLANLRMMRAAHT  299

292 IADEVGGVLDDQRRMMTPQKLREYQDII 320  SEQ ID NO:2
    ::|:|||:||    |:|||::
300 LAEDLQGVILTEEQEIFDANAEQAYLARV 328 SEQ ID NO:3
```

COMPOSITIONS AND METHODS FOR SCREENING ANTIMICROBIALS

FIELD OF THE INVENTION

The invention relates to screening compounds for antimicrobial activity, and, more particularly, to using bacterial proteins in vitro to detect compounds that interfere with cell division.

BACKGROUND

Antimicrobials are developed on the principle of selective toxicity. That is to say, antimicrobials, while toxic to the microorganism, must not be toxic to the patient. The selective toxicity of these drugs is usually relative, rather than an absolute. This means simply that most drugs are given to patients in concentrations that are tolerated by the patient, but are lethal or damaging to the microorganism; higher doses would be toxic to the patient and are avoided.

Selective toxicity is often a reflection of the presence of specific receptors present on the microorganism, but lacking in the host system. Other means to achieve selective toxicity commonly rely on the inhibition of biochemical events essential to the microorganism but not the host. As the physiology, structure, and biochemical systems of infectious agents and their hosts are usually quite different, antimicrobial development often relies on these differences.

Although the mechanisms of action of many antimicrobials are not well understood, the five major categories of action include inhibition of cell wall synthesis, inhibition of cell membrane function, inhibition of protein synthesis, inhibition of nucleic acid synthesis, and interference with intermediary metabolism. (See e.g., W. K. Joklik et aL, [eds.], *Zinsser Microbiology*, 18th ed., Appleton-Century-Crofts, Norwalk, Conn., [1984], p. 193). For example, penicillin, like all β-lactam drugs, is a compound which selectively inhibits bacterial cell wall synthesis. The initial step in the mechanism of action of these β-lactam drugs involves the binding of the drug to cell receptors known as "penicillin-binding proteins" ("PBP"). There are from 3–6 PBPs, with molecular weights ranging from $4-12\times10^5$; some of these PBPs are transpeptidation enzymes. (*Jawetz, Melnick & Adelberg's Medical Microbiology*, 19th ed, Appleton & Lange, Norwalk, Conn. [1991], p. 150). After binding to the PBP, the drug inhibits the transpeptidation reaction and synthesis of peptidoglycan in the organism's cell wall material is blocked. This results in the eventual triggering of an autolytic cascade which leads to cell lysis.

Because of their relatively high concentration of peptidoglycan, gram-positive organisms tend to be much more susceptible to the effects of penicillin and other β-lactams than gram-negative organisms. Importantly, because they affect cell wall synthesis, penicillin and the other β-lactams are only effective against actively growing and dividing cultures. However, one of the benefits of these β-lactam drugs is that animal cells do not have peptidoglycan; consequently, such drugs are remarkably non-toxic to humans and other animals.

Some organisms are naturally resistant to penicillin and the other β-lactams due to their lack of PBPs, the inaccessibility of the PBPs due to the presence of permeability barriers, the failure of autolytic cascades to be activated following binding of the drug, or the lack of peptidoglycan in the cell wall (e.g., the mycoplasmas, L-forms, and metabolically inactive bacteria). Unfortunately, following years of use to treat various infections and diseases, penicillin resistance has become increasingly widespread in the microbial populations that were previously susceptible to the action of these drugs. Some microorganisms produce β-lactamase, an enzyme which destroys the antimicrobial itself, while some microorganisms have undergone genetic changes which result in alterations to the PBPs, such that the drugs will no longer effectively bind to the receptors; still other organisms have evolved in a manner that prevents the lysis of cells to which the drug has bound. In this latter scenario, the drug has inhibited the growth of the cell, but it is not killed. In some circumstances this appears to contribute to the relapse of disease following premature discontinuation of treatment, as some of the cells remain viable and may begin growing once the antimicrobial is removed from their environment.

The development of tolerance and resistance to antimicrobials represents a significant threat to the ability to treat disease. Many factors have contributed to this increased observance of resistant strains, including over-use and/or inappropriate administration of antirnicrobials, the capability of many organisms to exchange genetic material which confers resistance (i.e., R plasmids), and the relatively rapid mutation rate observed with many bacteria, which allows for selection of resistant organisms.

One well-documented example which highlights the problems with development of penicillin resistance involves *Streptococcus pneumoniae*, a gram-positive organism. Initially, the introduction of penicillin to treat *S. pneumoniae* resulted in a significant decrease in the mortality due to this organism. However, *S. pneumoniae* remains of great concern, as it is one of the agents most frequently associated with invasive infections; it is the most common cause of bacterial pneumonia and otitis media; it is the second most common cause of bacterial meningitis; and it is the third most common isolate from blood cultures. (J. F. Sessegolo et al., "Distribution of Serotypes and Antimicrobial Resistance of *Streptococcus pneumoniae* Strains Isolated in Brazil From 1988 to 1992," J. Clin. Microbiol., 32:906–911 [1994]). Thus, the development of antimicrobial resistance in this organism is of great cause for concern.

The first report of pneumococci with decreased susceptibilities to penicillins occurred in 1967. Since this initial report out of Australia, additional strains with decreased susceptibilities have been reported worldwide. Additionally, resistance to penicillin alternatives, such as chloramphenicol, erythromycin, tetracycline clindamycin, rifampin, and sulfamethoxazole-trimethoprim has been reported, often in conjunction with penicillin resistance. Multiple-antimicrobial resistance in pneumococci was first reported in 1977. Since this initial report out of South Africa, multi-drug resistant strains have been reported in several countries, including Spain, Italy, France, Belgium, Hungary, Pakistan, Czechoslovakia, Canada, the United Kingdom, and the United States. (Sessegolo et al. supra, at 906).

In a survey conducted in Brazil, of 42 serotypes among 288 *S. pneumoniae* strains isolated during 1988–1992, Sessegolo et al. reported that decreased susceptibility to penicillin was detected in 26.7% of the strains. In addition, 35.9% of the strains were resistant to tetracycline, 29.2% were resistant to sulfamethoxazole-trirethoprim, 1.5% were resistant to rifampin, 0.80% were resistant to penicillin, and 0.50% were resistant to chloramphenicol. The penicillin-resistant strains were also found to be resistant to, or exhibited decreased susceptibility to cephalosporins. The resistance characteristics of these strains were also semi-quantitated, with intermediate resistances reported at 17.9% for penicillin, 8.7% for tetracycline, 6.7% for chloramphenicol, 6.1% for erythromycin, and 3.1% for rifampin.

Results obtained from patients in Rio de Janiero in 1981 and 1982, indicated that there was no penicillin resistance (relative or complete) in the pneumococcal isolates. However, during the period between 1988 to 1992, 19.4% of the strains from the same geographic population were relatively resistant, and 1.5% were completely resistant to penicillin. These results highlight the rapid spread of antimicrobial resistance.

Once an organism has developed resistance to a particular drug, it becomes important that an effective replacement drug be identified. If the organism develops resistance to this second drug, another replacement is needed. One example of the historical development of multiple drug resistance is gonorrhea. Prior to the 1930's, treatment for this disease usually involved mechanical means, such as irrigation and use of urethral sounds in males. In the late 1930's, sulfonamides were introduced and found to be effective in treating gonorrhea. After a few years, sulfonamide-resistant strains of N. gonorrhoeae were isolated. Fortunately, by this time, penicillin was available and found to be effective. However, by the 1970's, many isolates of N. gonorrhoeae were found to be penicillin-resistant. This required the use of alternative drugs such as spectinomycin. It can be expected that this trend will continue, with the development of strains that are resistant to sulfonamides, penicillin, spectinomycin, and other antimicrobials.

Thus, there remains a need to develop new antimicrobials. Ideally, the antimicrobial should target the physiology of the microorganism and demonstrate selective toxicity. However, the targeting should, nonetheless, allow for antimicrobial action against a broad spectrum of organisms. Most importantly, the antimicrobial should serve as an effective replacement drug for multiple-drug resistant organisms.

SUMMARY OF THE INVENTION

The invention relates to screening compounds for antimicrobial activity, and, more particularly, to using bacterial proteins in vitro to detect compounds that interfere with cell division. The present invention contemplates the use of the zipA gene and gene product for screening compounds for potential antimicrobial activity. Unlike current screening approaches, the screening approach of the present invention does not require the use of bacterial cells.

The present invention contemplates the over-expression of recombinant ZipA protein that is functional, and yet free of contaminating protein typically associated with traditional biochemical isolation techniques. The expression of recombinant ZipA protein of the present invention relies on the construction of vectors (e.g., plasmids) containing the zipA gene and suitable hosts for protein expression. It is not intended that the present invention be limited by the expression system chosen for the expression of recombinant zipA. The present invention contemplates all forms and sources of expression systems (i.e., an expression vector/host cell combination).

In one embodiment, the present invention contemplates a method for screening compounds, comprising: a) providing: i) a test compound; ii) a first protein, said first protein encoded by an oligonucleotide comprising at least a portion of the zipA gene; iii) a second protein capable of binding to said first protein; and iv) means for detecting said binding; b) mixing said first and second proteins in the presence of said test compound; and c) detecting binding using said means for detecting binding.

The method may be performed using immobilized elements and the immobilization may be carried out using a variety of immobilization means (e.g., columns, beads, adsorbents, nitrocellulose paper, etc.). In order to screen large libraries of test compounds (e.g., drugs, new antimicrobials, etc.), the screening assays of the present invention are preferably conducted in a microplate format.

The present invention contemplates a variety of assay formats. In one embodiment, said first protein (encoded by an oligonucleotide comprising at least a portion of the zipA gene) is immobilized. In another embodiment, said second protein (capable of binding to said first protein) is immobilized. In one embodiment, said second protein is FtsZ. In one embodiment, said second protein is labelled (e.g., radiolabelled).

It is not intended that the invention be limited by the means or method of detection. For example, the detection means might be a plate reader, a scintillation counter, a mass spectrometer or fluorometer.

It is not intended that the invention be limited by the nature of test compounds. Such compounds may be synthetic compounds or naturally available compounds.

The method of the present invention is particularly useful for identifying antimicrobials effective against bacteria. However, such identified drugs may have activity against other single cell and multicellular organisms, including, but not limited to fungi, mycoplasma and protozoa.

DESCRIPTION OF THE FIGURES

FIG. 4 shows the nucleotide sequence of a portion of the E. coli chromosome which contains the entire zipA gene. The nucleotide sequence of the zipA gene is provided (SEQ ID NO: 1) as well as the amino acid sequence of the ZipA protein (SEQ ID NO:2).

FIG. 5 shows the amino acid sequence of the ZipA protein homologue in H. influenzae (SEQ ID NO:3) aligned with the amino acid sequence of the ZipA protein in E. coli (SEQ ID NO:2).

DEFINITIONS

Figure 1:
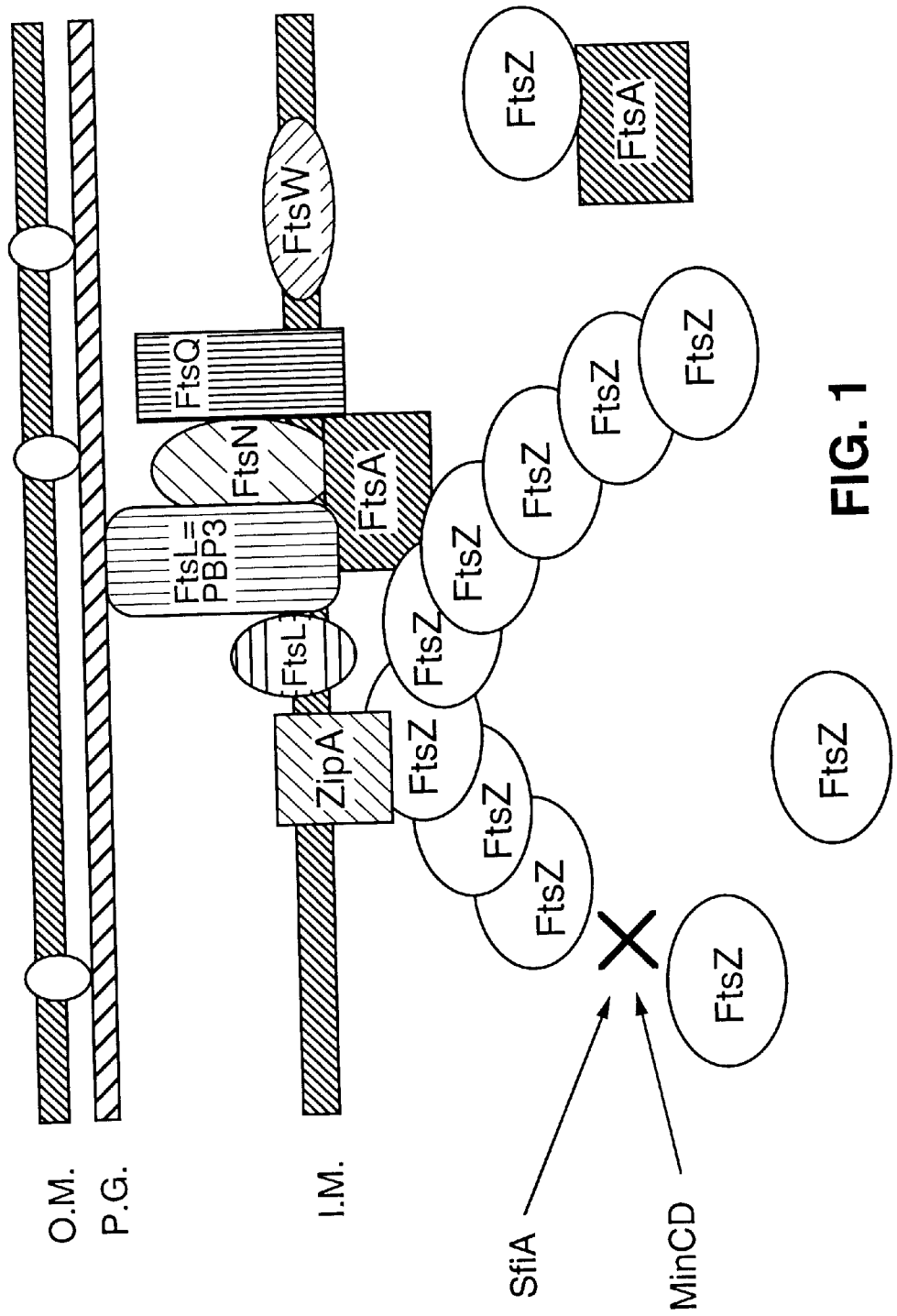
FIG. 1 schematically shows proteins involved in bacterial cell division that are contemplated to be useful in the present invention for screening antimicrobials.

To facilitate understanding of the invention, a number of terms are defined below.

As used herein, the term "vector" is used in reference to nucleic acid molecules that transfer DNA segment(s) from one cell to another. The term "vehicle" is sometimes used interchangeably with "vector." Commonly employed vectors include, but are not limited to, plasmids and bacteriophage vectors.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in procaryotes usually include a promoter, an operator (optional), and a ribosome binding site, often along with other sequences. Eukaryotic cells are known to utilize promoters, enhancers, and termination and polyadenylation signals.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids'bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids. Hybridization and the strength of hybridization (ie., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl. (See e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "amplifiable nucleic acid" is used in reference to nucleic acids which may be amplified by any amplification method, including but not limited to the polymerase chain reaction (PCR). It is contemplated that "amplifiable nucleic acid" will usually comprise "sample template."

As used herein, the term "sample template" refers to nucleic acid originating from a sample. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, which is capable of hybridizing to another oligonucleotide of interest. Probes are useful in the detection, identification and isolation of particular gene sequences.

It is contemplated that proteins (or probes) used in the present invention will be labelled with a "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label, whether a radioisotope, enzyme and flurogenic substance or other type of molecule (e.g., biotin, etc.). There are a number of commercially available kits to take advantage of particular labelling schemes (one such kit being available from Amersham and described in U.S. Pat. No. 4,568,649, hereby incorporated by reference).

As used herein, the term "target" refers to the region of nucleic acid bounded by the primers used for detection and/or amplification (e.g., by the polymerase chain reaction). Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleoside triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a DNA sequence comprising the coding region of a gene or in other words the DNA sequence which encodes a gene product. The coding region may be present in either a cDNA or genomic DNA form. Suitable control elements such as promoters and/or enhancers, splice junctions, polyadenylation signals, etc., may be placed in close proximity to the coding region of the gene if needed to permit proper initiation of transcription and/or correct processing of the primary RNA transcript in eukaryotic host cells. When prokaryotes are used as the host cell, suitable control elements may include but are not limited to promoters, operators, ribosome binding sites, and transcription termination elements. When expression is desired in a prokaryotic host, the coding region employed will typically lack introns. Alternatively, the coding region utilized in the expression vectors of the present invention may contain endogenous enhancers/promoters, splice junctions, intervening sequences, polyadenylation signals, etc., or a combination of both endogenous and exogenous control elements.

As used herein, the terms "nucleic acid molecule encoding," "DNA sequence encoding," and "DNA encoding" refer to the order or sequence of deoxyribo-nucleotides along a strand of deoxyribonucleic acid. The order of these deoxyribonucleotides determines the order of amino acids along the polypeptide (protein) chain. The DNA sequence thus codes for the amino acid sequence.

The term "drug" as used herein, refers to any medicinal substance used in humans or other animals. Encompassed within this definition are compound analogs, naturally occurring, synthetic and recombinant pharmaceuticals, hormones, antimicrobials, antibiotics, etc.

DESCRIPTION OF THE INVENTION

The invention relates to screening compounds for antimicrobial activity, and, more particularly, to using bacterial proteins in vitro to detect compounds that interfere with cell division. The present disclosure describes the isolation of the gene encoding the ZipA protein. An expression vector comprising a plasmid has been constructed to allow for the protein to be functionally over-expressed in bacterial cells. However, the plasmid also is constructed to be functionally over-expressed in other hosts. Indeed, it is not intended that the present invention be limited by the expression system; the present invention contemplates all forms and sources of expression systems.

In one embodiment, the present invention contemplates using the ZipA protein in a cell-free assay to screen compounds for their antimicrobial activity. The cell-free assay has inherent advantages over traditional antimicrobial screening assays.

In another embodiment, the present invention contemplates using the ZipA protein in a cellular assay. One cellular assay contemplated is the yeast two-hybrid system.

I. TRADITIONAL ANTIMICROBIAL SCREENING

To understand the limitations of cell-based screening assays (and the advantages of the cell-free screening assay of the present invention), it is useful to consider the principles inherent for the detection of cell growth. For example, a bacterial culture may be considered "sterilized" if an aliquot of the culture does not grow when transferred to fresh culture media (e.g., solid or liquid culture media) and placed under suitable conditions such that growth of the organism may occur. The time period and the growth conditions (e.g., temperature) may be referred to as an "amplification factor." This amplification factor, along with the limitations of the detection method (e.g., visual inspection of the culture plate for the appearance of bacterial colonies) define the sensitivity of the inactivation method. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the method appears to be completely effective (and above which the method is, in fact, only partially effective).

This interplay between the amplification factor of an assay and the threshold that the detection method defines, can be illustrated. For example, bacterial cells can be applied to a plate of culture media; the detection method is arbitarily chosen to be visual inspection. Assume the growth conditions and time are such that an overall amplification of $10^4$ has occurred. The detectable signal will be proportional to the number of bacterial cells actually present after amplification. For calculation purposes, the detection threshold is taken to be $10^6$ cells; if fewer than $10^6$ cells are present after amplification, no cell colonies are visually detectable and the inactivation method will appear effective. Given the amplification factor of $10^4$ and a detection threshold of $10^6$, the sensitivity limit would be 100 bacterial cells; if less than 100 viable bacterial cells were present in the original aliquot of the bacterial culture after the sterilization method is performed, the culture would still appear to be sterilized.

Such a situation is common for bacterial growth assays. The sensitivity of the assay is such that viable bacterial cells are present but the assay is unable to detect them.

Antimicrobial susceptibility testing using cell growth assays is one method to determine the effectiveness of an antimicrobial against a microorganism. Antimicrobial susceptibility is measured in vitro, in order to determine the toxicity (i.e., potency) of the antimicrobial in solution, estimate its concentration in body tissues or fluids, and determine the sensitivity of a given organism to known concentrations of the antimicrobial. There are various factors which may significantly affect the activity of antimicrobials in vitro. Such factors as the pH of the testing environment, the medium upon which the microorganisms were grown, the stability of the antimicrobial, the inoculum size, length of exposure to the antimicrobial, and the metabolic activity of the microorganisms must be taken into account during the in vitro testing of antimicrobial susceptibility. (See e.g., G. F. Brooks, et al., *Jawetz, Melnick & Adelberg's Medical Microbiology*, 19th ed, Appleton & Lange, Norwalk, Conn. [1991], p.155).

In many cases, it is possible to quantitate the amount or concentration of antimicrobial required to kill or inhibit microorganisms, without harming the patient. Quantitation becomes critical in some situations, as illustrated by the situation where an organism that previously was susceptible to low concentrations of an antimicrobial develops resistance to that antimicrobial. In addition, it is often not possible to predict the susceptibility of a particular organism or isolate to a particular antimicrobial. (See e.g., J. J. Jorgensen and D. F. Sahm, "Antimicrobial Susceptibility Testing: General Considerations," in P. R. Murray et al. [eds.], *Manual of Clinical Microbiology*, 6th ed., ASM Press, Washington, D.C., [1995], p. 1277). For all these reasons, the present invention is not limited to a cell-based screening method. Rather, the present invention allows for a cell-free detection system that does not have the drawbacks associated with measuring parameters of live cells.

II. PROTEINS USEFUL IN THE PRESENT INVENTION

In one embodiment, the present invention contemplates a cell-free method for screening compounds for antimicrobial activity involves using bacterial proteins in vitro to detect compounds that interfere with cell division. Thus, the present invention contemplates bacterial proteins involved in cell division (see FIG. 1) as proteins useful in compound screening. One such protein is the essential division protein FtsZ, which is very well conserved among different species.

Immediately before the start of cell division, FtsZ becomes concentrated at the inner membrane into a ring-like structure at the prospective division site. (See FIG. 1). During septation, the diameter of the FtsZ ring becomes smaller as it remains at the leading edge of the invaginating cell wall. Although the FtsZ-ring is thought to be crucial for cell wall invagination, its precise role is not known. In one attractive hypothesis, the ring is a contractile element which causes the cytoplasmic membrane to move inwards. This, in turn, could trigger the septum specific murein synthetase PBP3 (FtsI) to back up the inward moving membrane with a rigid murein layer.

Experiments performed in vitro with purified FtsZ have shown that the protein is a GTPase with the ability to form large polymers in a nucleotide-dependent fashion. This is consistent with the idea that the FtsZ ring contains one large, or multiple smaller, polymer (s) consisting of GTP/GDP-bound FtsZ subunits. The FtsZ peptides from the three bacterial species of known sequence share a 13 amino-acid segment that is completely conserved and that includes a 7 amino-acid stretch almost identical to the highly conserved sequence among the α-, β- and γ-tubulins of eukaryotic cells. A single amino-acid substitution within the tubulin signature sequence of FtsZ leads to a failure to initiate septum formation in cells grown at elevated temperatures.

While it is not intended that the present invention be limited by precise mechanisms, it is believed that FtsZ needs to interact with several different molecules that play specific roles in one or more of the cell division processes. Genetic studies have suggested possible interactions between FtsZ and several other proteins. Moreover, there is solid physical evidence for an interaction between FtsZ and FtsA. Indeed, FtsA can be co-purified with FtsZ and vice versa.

Figure 2:
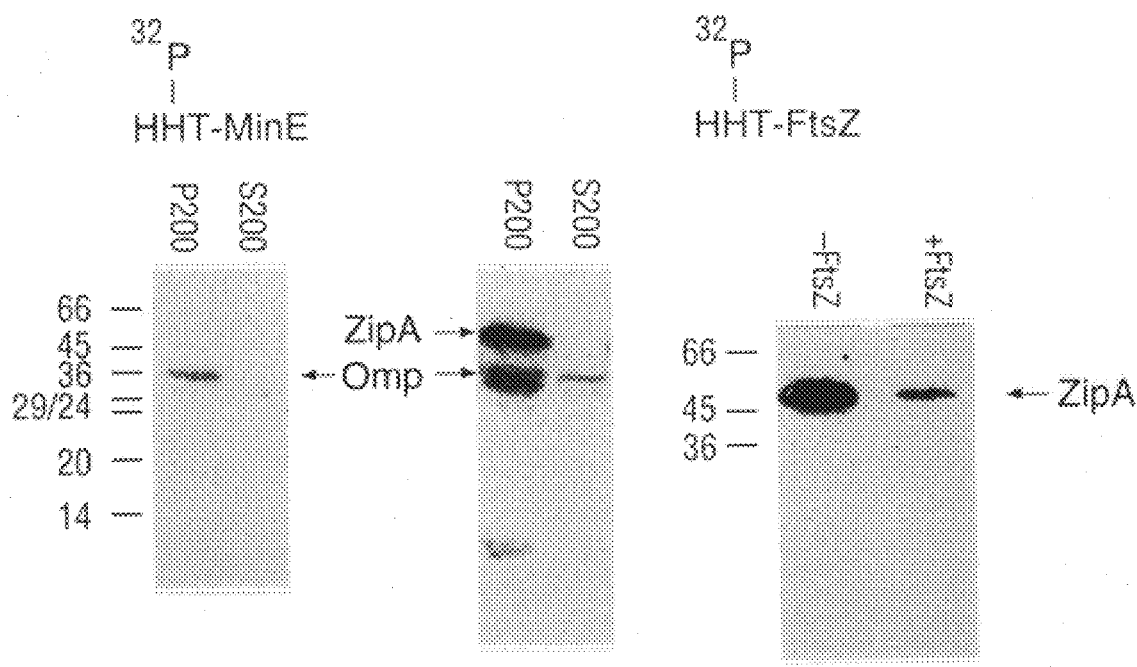
FIG. 2 is a audioradiograph of a binding assay using proteins immobilized on nitrocellulose.

To address the possibility that other proteins interact with FtsZ, the present inventors searched for proteins with affinity to FtsZ. In one approach, a FtsZ derivative (HFKT-FtsZ) was made which carries at the N-terminus a histidine-tag (the his-tag is useful for purification by metal chelate affinity chromatography such as that described in U.S. Pat, No. 5,310,663, hereby incorporated by reference) as well as a substrate site for heart muscle kinase. The purified protein was radiolabeled in vitro by incubation with kinase and $[\gamma^{32}P]ATP$ and used as a probe on Western blots. In this assay, HKFT-FtsZ bound specifically to one minor protein band present among the *E. coli* proteins found in the insoluble (P200) fraction (and not to any bands in the soluble (S200) fraction) corresponding to a species with an apparent MW of 50 Kd (see FIG. 2, middle panel), which the inventors have named "ZipA." Binding of the protein was specific for the FtsZ portion of the HKFT-FtsZ probe, since HKFT-tagged derivatives of several other proteins failed to bind to the 50 Kd band (the left-hand panel of FIG. 2 shows that radiolabelled HKFT-MinE binds Omp but not ZipA, thereby serving as a negative control) and since native FtsZ competes for binding [the right-hand panel of FIG. 2 shows decreased signal when native, unlabelled FstZ (indicated as "+FtsZ") is included in the assay].

ZipA was exclusively present in the insoluble fraction of broken cells. Treatment of this fraction with urea did not release ZipA, whereas treatment with either Sarkosyl or Triton X-100 efficiently solubilized the protein. This suggests that ZipA is an integral inner-membrane protein. While an understanding of the precise role of ZipA in cell division is unnecessary for the practice of the present invention, FIG. 1 schematically sets forth a possible arrangement for ZipA in relation to other known cell division proteins.

Figure 3:
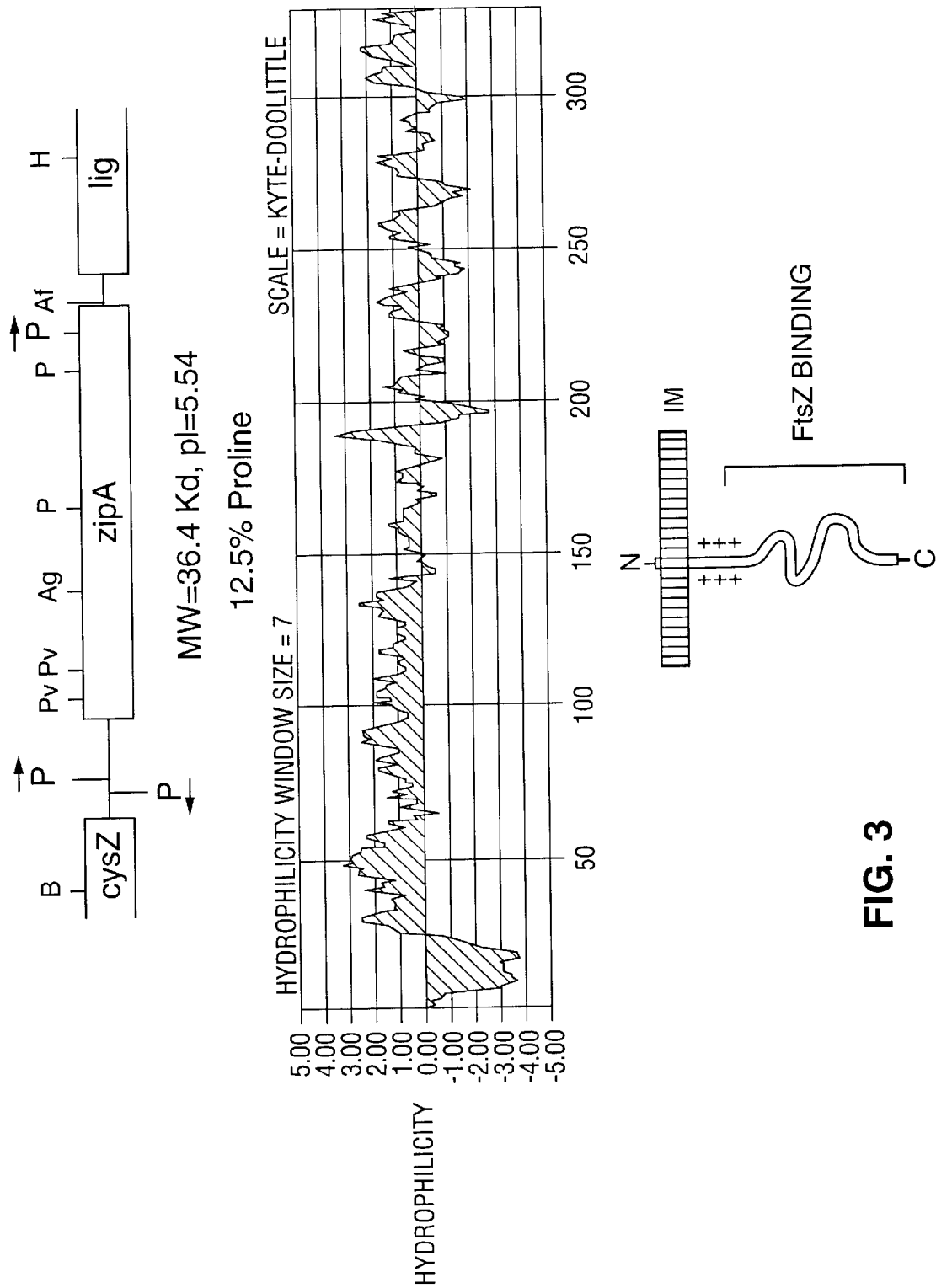
FIG. 3 schematically shows the location of the zipA gene on the E. coli chromosome, a hydrophilicity plot across the ZipA protein, and a schematic representation of ZipA within the inner membrane of a cell.
Figures 4, 4A, 4C, 4E:
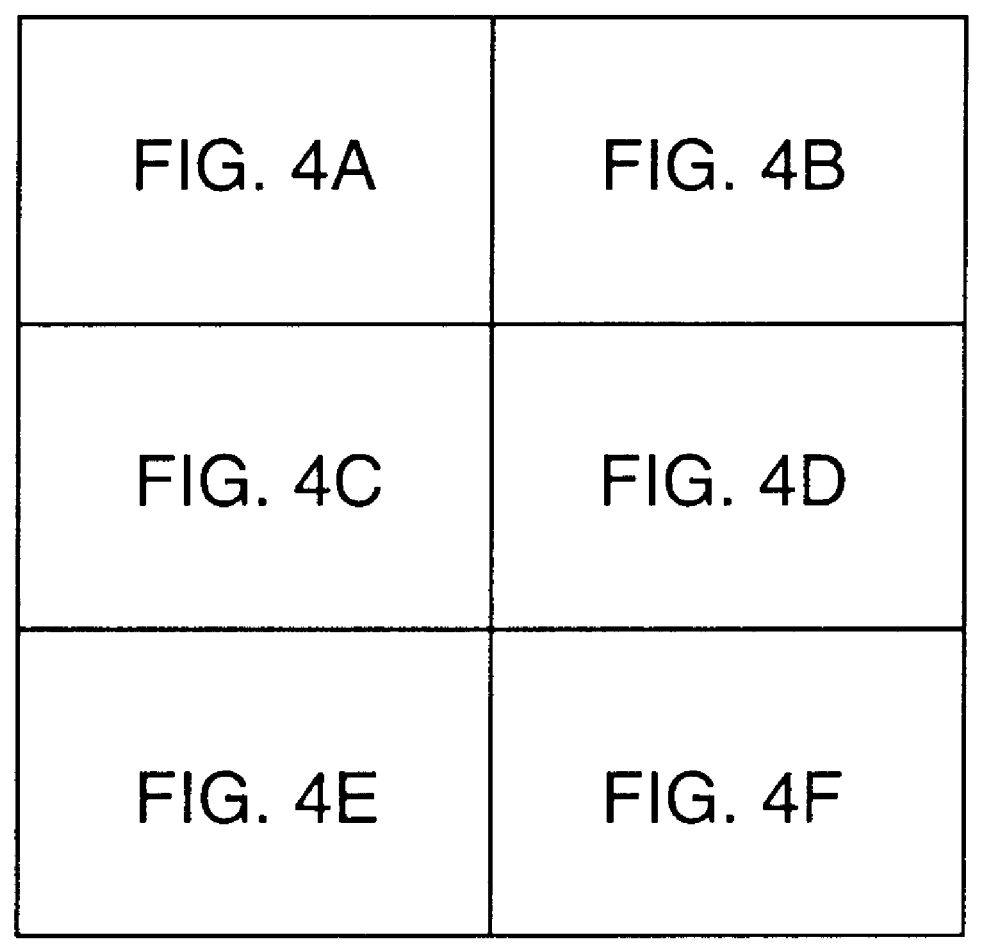

The gene for ZipA (zipA) was isolated by expression cloning from a λgt11 library, and shown to be a previously unidentified gene at 52 minutes on the *E. coli* chromosome. (See FIG. 3). Overexpression of the zipA open reading frame (ORF) in a T7 RNA polymerase based system led to overproduction of a single protein which migrated as a 50 Kd species, and which readily bound FtsZ in the assay described above. The predicted primary structure of ZipA shows aa hydrophobic N-terminus, and an abundance of proline residues (12.5%). The calculated MW is 36.4 Kd rather than 50 Kd indicating that the protein migrates aberrantly in SDS-PAGE gels. Database searches did not reveal any known proteins with significant similarity to ZipA. DNA fragments carrying the complete zipA gene could not be cloned on high copy number vectors, but could be maintained when carried on phage M13 or a low copy number plasmid. The nucleotide sequence of the zipA gene (SEQ ID NO:1) is shown in FIG. 4.

The ZipA protein should form an attractive basis for antimicrobial compound screens for several reasons, including but not limited to: 1) ZipA is essential, cells that lack sufficient ZipA activity die; 2) ZipA binds to FtsZ, even when either of the two proteins is (partially) denatured (in fact, ZipA was discovered by an affinity blotting technique in which radiolabeled FtsZ was used to probe Western blots of whole cell extracts that had been treated by boiling in detergent); 3) soluble fragments and derivatives of ZipA retain the ability to bind FtsZ [ie., a portion or fragment of the ZipA protein can be expressed (defined as the 39-328 peptide, see FIG. 4) as soluble protein (using the sequence of the zipA gene generated by digestion at the second PvuI site within the coding region) and this portion binds FtsZ]; 4) HFTK-ZipA will bind to native FtsZ as well as immobilized FtsZ; and 5) labelled derivatives of ZipA (e.g., in which a portion of the protein is fused to Green Fluorescent Protein) retain the ability to bind FtsZ.

The above-described features should make clear the great flexibility in the design of large screens for compounds that either interfere with the ability of FtsZ and ZipA to interact, or that bind to ZipA per se.

Antibodies

The present invention contemplates the use of antibodies, including the use of antibodies, in the screening assays. Such antibodies can be used either as a positive control (i.e., as antibodies that block interaction of ZipA with another protein) or as a binding partner for other proteins.

The antibodies directed to such proteins as ZipA and FtsZ or the ZipA:FtsZ binding complex ("primary antibodies") may be monoclonal or polyclonal. It is within the scope of this invention to include any secondary antibodies (monoclonal or polyclonal) directed to the primary antibodies discussed above. Both the primary and secondary antibodies may be used in the detection assays or a primary antibody may be used with a commercially available anti-immunoglobulin antibody. An antibody as contemplated herein includes any antibody specific to any region of a cell division protein.

Both polyclonal and monoclonal antibodies are obtainable by immunization with the protein and either type is utilizable for immunoassays. The methods of obtaining both types of antibodies are known in the art. Polyclonal antibodies are less preferred but are relatively easily prepared by injection of a suitable laboratory animal with an effective amount of the purified protein, or antigenic parts thereof, collecting serum from the animal, and isolating specific antibodies by any of the known immunoadsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are known to those who are skilled in the art. (See, for example, Douillard and Hoffman, Basic Facts about Hybridomas, in *Compendium of Immunology*, Vol. II, ed. by Schwartz, 1981; Kohler and Milstein, Nature 256:495–499, 1975; European Journal of Immunology 6:511–519, 1976).

Unlike preparation of polyclonal antibodies, the choice of animal for the isolation of sensitized lymphocytes is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with an antigenic amount, for example, from about 0.1 mg to about 20 mg of the protein or antigenic parts thereof. Usually the injecting material is emulsified in Freund's complete adjuvant. Boosting injections may also be required. The detection of antibody production can be carried out by testing the antibody with appropriately labelled antigen. Lymphocytes can be obtained by removing the spleen of lymph nodes of sensitized animals in a sterile fashion and then used to carry out fusion with the immortal cell line. Alternatively, lymphocytes can be stimulated or immunized in vitro, as described, for example, in Reading, Journal of Immunological Methods 53: 261–291, 1982.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1000 to 6000. Best results are obtained when the PEG is diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to choose a malignant line which is Hypoxthanine Guanine Phosphoribosyl Transferase (HGPRT) deficient, which will not grow in an aminopterin-containing medium used to allow only growth of hybrids and which is generally composed of hypoxthanine $1 \times 10^{-4}$M, aminopterin $1 \times 10^{-5}$M, and thymidine $3 \times 10^{-5}$M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxthanine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21–23 days of cell growth in selective medium (e.g., HAT). Cloning can be preformed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

Binding to the cell division protein contemplated herein may be accomplished in a number of ways such as on a semi-solid growth medium plate where colonies of bacteria are tested, by for example, the Western blotting procedure. Alternatively, other semi-solid supports may be employed onto which the sample containing the protein has been immobilized. In another method, the sample containing the protein is contacted with a solid support already containing a specific antibody. In any event the principle behind the assay is the same. A wide range of immunoassay techniques are available as can be seen in U.S. Pat. Nos. 4,016,043, 4,424,279 and 4,018,653, hereby incorporated by reference. This, of course, includes both single-site and two-site, or "sandwich", assays of the non-competitive types, as well as in the traditional competitive binding assays.

Sandwich assays are among the most useful and commonly used assays and are favored for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen secondary complex, a second antibody specific to the antigen, labelled with a reporter molecule capable of producing a detectable signal is then added and incubated, allowing time sufficient for the formation of a tertiary complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent.

In the typical forward sandwich assay, a first antibody having specificity for the enzyme or protein, or antigenic parts thereof, contemplated in this invention, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary but will generally be in the range of about 2–40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores, luminescent molecules or radionuclide containing molecules (ie., radioisotopes).

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicyclic acid, or toluidine are commonly used. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the tertiary complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescent and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

Analogues And Homologues

The present invention contemplates the use of analogues, and in particular ZipAk and FtsZ protein analogues. Such analogues are defmed as derivatives that have been modified structurally but that are observed to function in an analogous manner [e.g., continue to demonstrate detectable binding, ie., binding of approximately two fold (and more preferably approximately five fold) above the background binding of the negative control, under the conditions of the assays described herein (for example, using radiolabels and measuring counts per minute), albeit with different affinity than the parent (underivatized) molecule]. Those proteins that do not finction in an analogous manner are "non-ZipA" and/or "non-FtsZ" proteins. Protein analogues may be created by modification of the nucleotide sequence encoding the zipA and/or ftsZ genes (e.g., by substitution, deletion, etc.). Alternatively, the present invention contemplates the use of analogues generated by synthesis of polypeptides in vitro such as by chemical means (or in vitro translation of mRNA).

The present invention also contemplates the use of homologues, which are defined as the corresponding proteins for ZipA and FtsZ in other species, including both Gram positive and Gram negative species. In one embodiment, the present invention contemplates the use of homologous proteins from *Haemophilus influenzae* Rd, which is a small, nonmotile, Gram-negative bacterium whose only natural host is human. Six *H. influenzae* serotype strains (a through f) have been identified on the basis of immunologically distinct capsular polysaccharide antigens. Non-typeable strains also exist and are distinguished by their lack of detectable capsular polysaccharide. They are commensal residents of the upper respiratory mucosa of children and adults and cause otitis media and respiratory tract infections, mostly in children. More serious invasive infection is caused almost exclusively by type b strains, with meningitis producing neurological sequelae in up to 50% of affected children.

The genome size of *influenzae* Rd is typical among bacteria. More specifically, the *H. influenzae* Rd genome is a circular chromosome of 1,830,137 bp. The overall G+C nucleotide content is approximately 38% (A, 31% ; C, 19%; G, 19%; T, 31%). The G+C-rich regions correspond to six rRNA operons and a cryptic mu-like prophage. Genes for several proteins similar to proteins encoded by bacteriophage mu are located at approximately position 1.56 to 1.59 Mbp of the genome. This area of the genome has a markedly higher G+C content that average for *H. influenzae* (~50% percent G+C compared to ~38% for the genome overall).

The minimal origin of replication (oriC) in *E. coli* is a 245-bp region defined by three copies of a 13-bp repeat at one end (sites for initial DNA unwinding) and four copies of a 9-bp repeat at the other. An approximately 280-bp sequence containing structures similar to the three 13-bp and four 9-bp repeats defines the putative origin of replication in *H. influenzae* Rd. This region lies between sets of ribosomal operons rrnF, rrnE, rrnD and rrnA, rrnB, rrnC. These two groups of ribosomal operons are transcribed in opposite directions and the placement of the origin is consistent with their polarity for transcription.

Termination of *E. coli* replication is marked by two 23-bp termination sequences located ~100 kb on either side of the midway point at which the two replication forks meet. Two potential termination sequences sharing a 10-bp core sequence with the *E. coli* termination sequence have been identified in *H. influenzae*. These two regions are offset approximately 100 kb from a point approximately 180° opposite of the proposed origin of *H. influenzae* replication.

A homologue gene encoding ZipA in *H. influenzae* is located (as with *E. coli*) adjacent to the DNA ligase gene. FIG. 5 shows the amino acid sequence of the ZipA protein from *E. coli* (top sequence) aligned with the homologue from *H. influenzae* (bottom sequence) (SEQ ID NO:3). The alignment shown in FIG. 5 was generated using the Bestfit proghram (BLAST Network Servie, National Center for Biotechnology Information). Gaps were introduced to provide maximum alignment between the two sequences (dots within a strand indicate a gap). Vertical lines between the two sequences indicate regions of identity. A double dot indicates a conservative substitution, while a single dot between the strands indicates a less conservative substitution.

There are a number of regions of striking homology, including but not limited to:Ile Leu Ile Ile Val Gly (SEQ ID NO:4) Asp Leu Xaa Xaa Ile Leu Ile Ile Val Gly (SEQ ID NO:5); Ile Leu Ile Ile Val Gly Xaa Xaa Ala Xaa Xaa Ala Leu (SEQ ID NO:6); Ile Leu Ile Ile Val Gly Xaa Xaa Ala Xaa Xaa Ala Leu Xaa Val His Gly (SEQ ID NO:7); Ala Leu Xaa Val His Gly (SEQ ID NO:8); Ala Leu Xaa Val His Gly Xaa Trp (SEQ ID NO:9); Tyr His Arg His Leu (SEQ ID NO:10); Pro Xaa Leu Phe Ser Xaa Ala Asn (SEQ ID NO:11); Pro Gly Thr Phe (SEQ ID NO:12); Xaa Phe Met Gln (SEQ ID NO: 13); Xaa Phe Met Gln Xaa Pro Ser (SEQ ID NO:14); present invention contemplates ZipA protein homologues having one or more of these regions of homology.

DETAILED DESCRIPTION OF THE INVENTION

The detailed description of the invention is divided into five major sections: I) Gene Isolation and Plasmid Construction; II) Protein Expression and Purification; III) Protein Labelling; IV) Binding To Other Proteins; and V) Antimicrobial Screening.

I. Gene Isolation And Plasmid Construction

Figure 6:
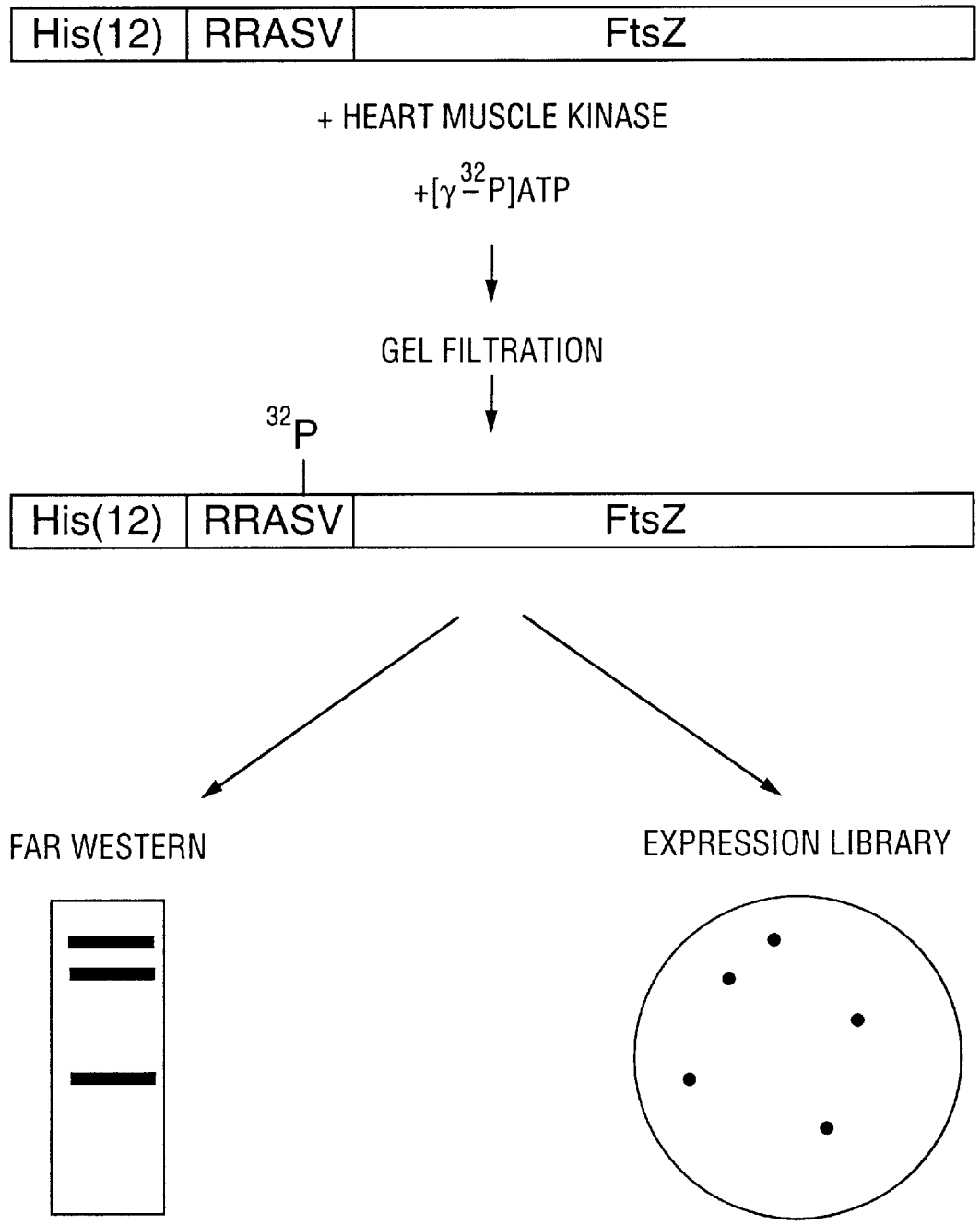
FIG. 6 schematically shows the expression cloning utilized in the present invention.

Isolation of the *E. coli* zipA gene and construction of plasmids containing the zipA gene was performed as generally described by Sambrook et al., *Molecular Cloning, A Laboratory Manual*, 2nd Ed., (Cold Spring Harbor Press, N.Y. 1989). The zipA gene was isolated by expression cloning [schematically represented in FIG. 6; FIG. 6 shows that the labelled FtsZ fusion protein can be used to probe an expression library to identify recombinant clones expressing proteins which bind to FtsZ ("Expression Library")as well as to probe Western blots to identify protein species separated by electrophoresis which bind to FtsZ ("Far Western")]. Briefly, a λgt11 library was made from chromosomal DNA of *E. coli* strain PB103. Plaques were lifted to nitrocellulose filters and probed with $^{32}$P-labelled HKFT-FtsZ to identify clones capable of expressing ZipA (the expression, purification and labelling of HKFT-FtsZ is described below). In total 7 recombinant phage were identified, all of which contained 7–10 Kb of *E. coli* DNA, including the complete zipA gene. The nucleotide sequence of the zipA gene is listed in SEQ ID NO:1 and the amino acid sequence of the ZipA protein is listed in SEQ ID NO:2.

Figure 7:
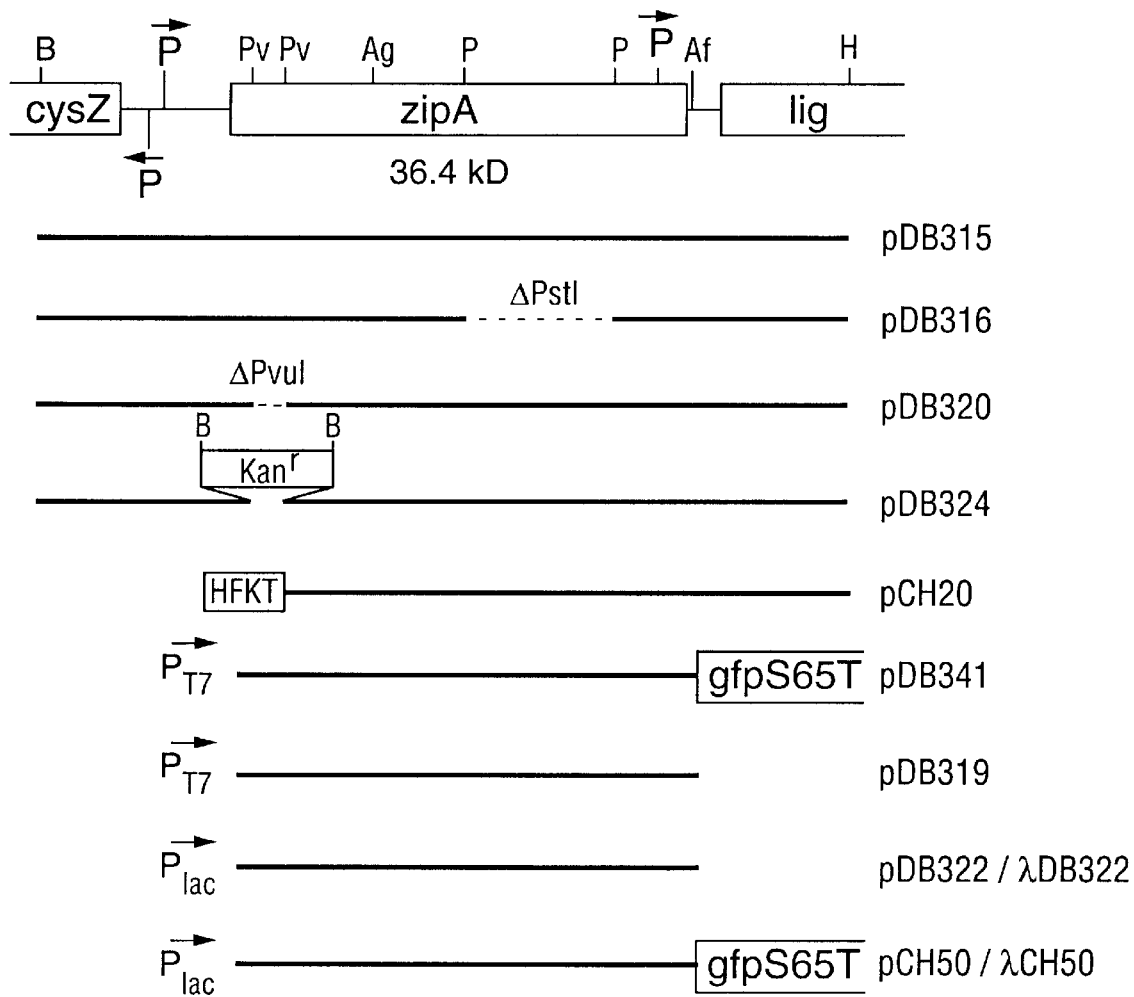
FIG. 7 schematically shows a number of plasmid constructs containing zipA sequences.

FIG. 7 shows a portion of the *E. coli* genome containing the zipA gene which was present on the recombinant phage clones. As shown at the top of FIG. 7, the zipA gene is located between the cysZ gene and the lig gene, the latter encoding DNA ligase. In FIG. 7, the following abbreviations are used: B (BamHI), Pv (PvuI), Ag (AgeI), P (PstI), Af (AflII), H (HindIII). The large P under an arrow indicates the location of the promoter driving the expressing of either the cysz, zipA or lig genes; the direction of the arrowhead indicates the direction of transcription. The DNA sequence found between the BamHi and HindIII sites shown at the top of FIG. 7 which contains the complete zipA gene as well as portions of the cysZ and lig genes is listed in SEQ ID NO:1 and shown in FIG. 1. A number of plasmid constructs containing zipA sequences are shown schematically in FIG. 7 (only sequences containing zipA sequences are depicted; ie., the plasmid backbone is not depicted). pDB315 contains a 1727 bp BamHI-HindIII fragment containing the entire zipA gene and portions of the cysZ and lig genes; this BamHI-HindIII fragment was isolated from one of the seven λgt11 clones. The generation of pDB3 15 and the remaining plasmids is discussed below.

To permit over-expression of the ZipA protein in bacterial cells, the complete zipA ORF was inserted into the pET21b vector which allowed the expression of ZipA under the control of the T7 promoter; the resulting plasmid was termed pDB319. The construction of pDB319 and a number of plasmids which encode fragments of the ZipA protein is describe below. In addition, the construction of vectors encoding fusion proteins which are employed in the screening methods of the present invention are also described.

a) Construction Of Vectors Encoding The ZipA Protein And Fragments Thereof

Plasmids pDB319 and pDB322 express the complete zipA gene under the transcriptional control of the T7 or lac promoter, respectively. To construct pDB319 and pDB322, zipA was amplified by a PCR with primers 5'-ACAGAGATCCAT<u>ATGA</u> TGCAGGATTTGCGTCTG-3' (SEQ ID NO:15) and 5'-TTAACCAAGCTTAAGTGT ATCAGGCGTTGG-3' (SEQ ID NO:16) designed to introduce a NdeI site at the translation start codon (underlined) of zipA. Chromosomal DNA isolated from E. coli strain PB103 was used as template. The 1018 bp PCR product was treated with HindIII and NdeI, and the resulting 986 bp fragment was ligated to pET21a (Novagen) which had been digested with HindIII and NdeI to generate pDB317.

The 676 bp AgeI-HindIII fragment of pDB317 was then replaced with the 1015 bp AgeI-HindIII fragment of pDB315 (described below), yielding pDB318. To obtain pDB319, pDB318 was treated successively with AflII and HindIII, Klenow enzyme plus deoxynuceotides, and ligase, thereby removing all lig sequences and retaining a HindIII site. Plasmid pDB319 encodes the complete ZipA protein under the control of the T7 promotor. To place zipA expression under control of the lac promotor, the 1089 BglII-HindIII fragment of pDB319 was ligated to BamHI-HindIII-digested pMLB1113, yielding pDB322 [the pMLB plasmids are derived from pBR322 and carry a polylinker region flanked on one side by the lacI gene, the lac promotor and operator, and the lacZ ribosome binding site and translation start codon, and on the other side by the rest of the lacZ gene and part of lacY; the plasmids also contain the beta-lactamase gene for ampicillin resistance].

Plasmids encoding fragments of ZipA were constructed as follows. For pDB315 and pDB316, the 1727 bp BamHI-HindIII fragment from the λgt11 derivative λCH1-1A (zipA$^+$) (i.e., one the original λgt11 clones) was first inserted in M13mp19 (Pharmacia), yielding M13mp19H-B1.7. A 338 bp deletion within zipA was created by digestion of M13mp19H-B1.7 DNA with PstI, and recirculation of the large fragment, resulting in M13mp19H-B1.7ΔPstI. The 1727 bp and 1389 bp BamHI-HindIII fragments from the two phages were next cloned into pMAK700 [this vector was chosen to be able to introduce a knock-out of the zipA gene in the chromosome;

pMAK700 is a pSC101 derivative but contains a repAts allele which renders the plasmid temperature sensitive for replication, as well as a chloramphenicol resistance marker], yielding pDB315 (zipA$^+$) [which contains the complete zipA gene] and pDB316 (zipA$^-$) [which contains the same fragment but with a 330 bp PstI fragment, internal to zipA, deleted (thus zipA–)], respectively.

b) Construction Of Plasmids Encoding ZipA/GFP Fusion Proteins

The present invention contemplates "fusion labelling" of the proteins useful in the screening method. In one embodiment, the present invention contemplates a fusion protein comprising ZipA (or a portion thereof) and the green fluorescent protein (GFP) from the jellyfish Aequorea Victoria. GFP emits green light (approximately 510 nm). Unlike other bioluminescent reporters, GFP fluoresces in the absence of any other proteins, substrates, or cofactors.

Purified GFP is a 27-kDa monomer consisting of 238 amino acids. While intact GFP is required for fluorescence, the active chromophore is a hexapeptide which contains a cyclized Ser-dehydroTyr-Gly trimer. Chromophore formation is oxygen-dependent and occurs gradually after translation.

GFP-containing vectors are commercially available from Clontech Laboratories, Inc. (Palo Alto, Calif.) (hereinafter "Clontech"). pGFP (Clontech) is primarily intended as a source of the GFP cDNA, which can be readily excised using restriction enzyme sites in the two multiple cloning sequences (MCS) flanking the gfp coding sequences. Alternatively, the GFP coding sequences can simply be amplified from any plasmid containing the GFP gene by PCR. pGFP-1 (Clontech) is a versatile transcription reporter vector for monitoring the activity of promoters cloned into the MCS upstream of the promoterless GFP gene. The sequences around the GFP start codon have been converted to a Kozak consensus translation initiation site to increase translation efficiency in eukaryotic cells. The vector also contains a neomycin/kanamycin-resistance cassette for selection for selection of transformed bacterial and eukaryotic cells. pGFP-N1 is one of three vectors which are useful for fusing heterologous proteins to the N-terminus of GFP. The same MCS is present in a different reading frame in pGFP-N1, pGFP-N2, and pGFP-N3. These constructs enable the use of an), one of 17 restriction sites to create an in-frame fusion to a convenient restriction site in the gene of interest. Similarly, pGFP-C1, pGFP-C2, and pGFP-C3 (Clontech) can be used to create in-frame fusions to the C-terminus of GFP. All six GFP protein fusion vectors contain the Kozak consensus sequence, the immediate early promoter of cytomegalovirus (CMV) to express fusions in mammalian cells, and a neomycin/kanamycin-resistance cassette.

Plasmids pDB341 and pCH50 (shown schematically in FIG. 7) encode ZipA/GFP fusion proteins. For pDB341 and pCH50, zipA was amplified by a PCR as above, except that the downstream primer used was 5'-AAGT<u>CTCGAG</u>GGCGTTGGC GTCTTTGAC-3' (SEQ ID NO:17). This primer was designed to substitute the translation stopcodon with an XhoI site (underlined). The PCR product was treated with NdeI and XhoI, and the 984 bp fragment ligated to NdeI and XhoI-digested pET21b, resulting in pCH38. Plasmid pGFPS65T is a mutant derived from pGFP by substituting a serine at position 65 for a threonine; the plasmid contains gfpS65T on a 729 bp BamHI fragment in the vector pRSET B (available commercially from Invitrogen, Madison, Wis.). This fragment was ligated to BamHI-digested pET16b yielding plasmid pDB338 which contains an XhoI site immediately upstream of the gfp coding sequence. The small ApaI-XhoI fragment of pDB338 was next replaced by that of pCH38, resulting in pDB341 [PT7::ZipA-GfpS65T]. This plasmid encodes a 64.2 kd ZipA-GfpS65T fusion protein which includes the complete ZipA and Gfp proteins, fused by a small linker peptide (LEDPPAEF) (SEQ ID NO: 18). To place expression of this fusion under control of the lac promotor, the ~2180 bp BglII-HindIII fragment of pDB341 was next inserted into the BamHI and HindIII sites of pMLB1113, yielding pCH50 [$P_{lac}$::ZipA-GfpS65T].

c) Construction Of Plasmids Encoding MinE And FtsZ Fusion Proteins

Plasmids encoding fusion proteins comprising the MinE and FtsZ proteins were constructed to allow the over-expression of these proteins used to provide negative and positive controls respectively in the methods of the present invention. As the MinE protein does not interact with the ZipA protein, it is useful as a negative control. In contrast, the FtsZ protein interacts with the ZipA protein, and it is useful as a positive control.

i) Plasmids Encoding MinE Fusion Proteins pDB311 encodes a 15.9 kD HFKT-MinE fusion protein, in which the N-terminal four amino acids of MinE are replaced with the HFKT peptide Met Gly His His His His His His His His His His Ser Ser Gly His Ile Glu Gly Arg His Met Asp Tyr Lys Asp Asp Asp Asp Lys Ala Arg Arg Ala Ser Val Glu Phe His Met Ala Ser Met Thr Gly Gly Gln Gln Met Gly Arg Gly Ser (SEQ ID NO:19); under control of the T7 promoter. To construct plasmid pDB311, pDB151 was treated successively with TaqI, Klenow enzyme plus deoxynucleotides, and EcoRI. The 307 bp fragment, coding for all but the first four amino acids of MinE, was ligated to pET21a (Novagen) that had been treated successively with BamHI, Klenow enzyme plus deoxynucleotides, and EcoRI. This yielded pDB302, in which the BamHI site was restored as expected, but the EcoRI site was fortuitously destroyed. Plasmid PDB302 encodes a T7.tag-MinE (T-MinE) fusion protein, in which the N-terminal four amino acids of MinE are replaced with the T7.tag peptide Met Ala Ser Met Thr Gly Gly Gln Gln Met Gly Arg Gly Ser (SEQ ID NO:20), under control of the T7 promoter of the vector.

The 1037 bp ApaI-NdeI fragment of pDB302 was replaced with the 1099 bp ApaI-NdeI fragment of pET16b (Novagen). The resulting plasmid, pDR1, encodes a fusion protein, HT-MinE in which the His-tag peptide Met Gly His His His His His His His His His Ser Ser Gly His Ile Glu Gly Arg His (SEQ ID NO:21) is fused to the N-terminus of the T-MinE protein. Plasmid pAR(ΔRI)59/60 [see generally, M. A. Blanar and W. J. Rutter, "Interaction Cloning: Identification of a helix-loop-helix Zipper Protein that Interacts with cFos," Science 256:1014 (1992)] contains a 54 bp NdeI fragment encoding the peptide Met Asp Tyr Lys Asp Asp Asp Asp Lys Ala Arg Arg Ala Ser Val Glu Phe (SEQ ID NO:22). This peptide, denoted as FK, is a fusion of the Flag peptide (IBI) with a Heart Muscle Kinase substrate peptide (underlined). To ease the manipulation of the NdeI cassette, a ~1800 bp EcoRI fragment, isolated from pUC4-KIXX (Pharmacia) and carrying the Tn5 aph(neo) gene, was inserted in the EcoRI site of pAR(ΔRI)59/60 which is flanked by the NdeI sites. The ~1850 bp NdeI fragment of the resulting plasmid, pTD1, was next inserted in the NdeI site of pDR1, yielding pDB309. Finally, pDB311 was obtained by deletion of the ~1800 bp Tn5 stuffer-fragment by treatment with EcoRl and re-ligation.

ii) Plasmids Encoding FtsZ Fusion Proteins

Plasmid pDR10 encodes a 46.6 kD HFKT-FtsZ fusion protein in which the peptide Met Gly His His His His His His His His His His Ser Ser Gly His Ile Glu Gly Arg His Met Asp Tyr Lys Asp Asp Asp Asp Lys Ala Arg Arg Ala Ser Val Glu Phe His Met Ala Ser Met Thr Gly Gly Gln Gln Met Gly Arg Gly Ser His (SEQ ID NO:23) is fused to the complete FtsZ protein.

To construct plasmid pDR10, chromosomal DNA from E. coli strain PB103 [see generally, P.A.J. de Boer et al., "Isolation and Properties of minB, a Complex Genetic Locus Involved in Correct Placement of the Division Site in Escherichia coli" J. Bacteriol. 170:2106 (1988)] was used as a template in a PCR to amplify ftsZ. Primers [5'-GGAGGATCCCAT<u>ATG</u>TTTGAACCAATGGAAC-3' (SEQ ID NO:24) and 5'-TTCCGGTCGACTCTTAATCAGCTTGCTTACG-3' (SEQ ID NO:25)] were designed to introduce a BamHI site near the translation start codon (underlined) of ftsZ. The resulting 1176 bp PCR product was treated with BamHI and SalI to yield a 1163 bp fragment which was used to replace the 320 bp BamHI-SalI fragment, containing all minE sequences, from pDB311. The resulting plasmid was termed pDR10.

II. Protein Expression And Purification

MinE and FtsZ fusion proteins (both containing the HFKT peptide) were expressed in E. coli and purified as follows. Strain HMS174(DE3)/pLysS (Novagen) was transformed with either pDR10 or pDB311. HMS174(DE3)/pLysS containing either pDR10[PT7::hfkt-ftsZ] or pDB311 [PT7::hfkt-minE] were grown shaking overnight at 37° C. in LB medium with ampicillin (100 µg/ml), chloramphenicol (25 µg/ml) and glucose (0.2%). Cultures were diluted 200× in 500 ml of LB with 50 µg/ml ampicillin and 0.04% glucose. At an $OD_{600}$ of approximately 0.5, IPTG (isopropyl-β-thiogalactoside) was added to 0.84 mM, and growth was continued for 90 min. Cells were collected by centrifugation (5000×g) and washed once in 20 ml of cold saline 0.9% NaCl. Pellets were quickly frozen in a dry-ice/acetone bath and stored at −85° C. Cells were quickly thawed at 37° C., and resuspended in 5.0 ml of cold buffer A (20 mM Tris.Cl, 70 mM NaCl, 50 mM imidazole, pH 7.9). Cell lysis was induced by three additional cycles of rapid freezing (dry-ice/acetone bath) and thawing (37° C. waterbath).

The lysate was briefly sonicated to reduce viscosity, and insoluble material was removed by centrifugation at 200,000×g for 3 hr at 8° C. A portion of the supernatant (50 mg total protein) was passed 3 times over a 0.5 ml Fast Flow Chelating Sepharose (Pharmacia) column, which had previously been charged with $NiSO_4$ and equilibrated in buffer A. The column was washed 3 times with 1.5 ml of buffer B (20 mM Tris-Cl, 500 mM NaCl, 50 mM imidazole, pH 7.9), and 3 times with 1.0 ml of buffer C (20 mM Tris-Cl, 500 mM NaCl, 200 mM imidazole, pH 7.9). The HFKT-tagged protein was then eluted in 3×1.0 ml of buffer D (20 mM Tris-Cl, 500 MM NaCl, 500 mM imidazole, pH 7.9). Appropriate fractions (determined by SDS PAGE) were pooled, dialyzed extensively against buffer E (20 mM Tris-Cl, 25 mM NaCl, 2 mM EDTA, pH 8.0), concentrated in a Centricon 10 device (Amicon), and stored frozen at −85° C. The HFTK-tagged proteins were estimated to be greater than 95% pure as judged by SDS-PAGE and Coomassie Brilliant Blue staining (approximately 25 micrograms of protein were loaded on a 12% acrylamide gel).

III. Protein Labelling

The purified HFKT-tagged proteins were phosphorylated in vitro by incubation with [$\gamma^{32}P$]ATP and the catalytic subunit of bovine heart muscle kinase (Sigma Chemical Co., St. Louis, Mo.). Reactions (30 µl) were performed on ice for 45 min, and contained HMK-buffer (20 mM Tris-Cl, 100 mM NaCl, 12 mM $MgCl_2$, 1 mM DTT, pH 7.5), 300–600 pmol (9–15 µg) purified HFKT-tagged protein, 60 µCi [γ-$^{32}$P]ATP (6000 Ci/mmol), and 1 µl of kinase (10 U/µl in 40 mM DTT). To separate protein from other reaction components, 20 µl of buffer Z (25 mM HEPES-KOH, 100 mM KCL, 12 mM MgCl$_2$, 1 mM DTT, 10% glycerol, pH 7.7) was added, and the mixture was loaded onto a 2.0 ml Kwiksep Excellulose desalting column (Pierce), which had previously been washed with 5.0 ml of buffer Z containing 1 mg/ml BSA (bovine serum albumin), and 5.0 ml of buffer Z without BSA respectively. The excluded volume was collected in fractions of 50 µl, and aliquots were used to determine radioactivity by scintillation counting. To visualize the presence and integrity of the desired radiolabeled species, aliquots were electrophoresed on SDS-PAGE gels followed by autoradiography of dried gels. Peak fractions were pooled and kept on ice until further use. Typical specific activities obtained were 1.5 to 4.0×10$^6$ cpm/µg HFKT-MinE and 5.0 to 8.0×10$^6$ cpm/µg HFKT-FtsZ.

IV. Use Of Immoblized Fusion Proteins In Binding Assays

Affinity Blotting

After the addition of one volume of electrophoresis sample buffer (125 mM Tris.Cl, 4% SDS, 20% glycerol, 1.4 M β-mercaptoethanol, pH=6.6), samples (e.g., whole cells boiled in sample buffer, or fractionated cells) were held in a boiling water bath for 5 min., and subjected to conventional SDS-PAGE on 0.75 mm thick 10%T/2.7%C gels. Electrophoretic transfer to nitrocellulose filter (0.2 µ) was performed in a Genie blotter (Idea Scientific Co.) with regular Towbin buffer (25 mM Tris.Cl, 192 mM glycine, 20% methanol, pH 8.3) at 12 V for 30 min. To monitor the transfer and to visualize the molecular weight standards, filters were treated with the reversible stain Ponceau S (0.1% in 5% acetic acid) for 1 min. Filters were next destained in 10 mM Tris-Cl, rinsed in water, and allowed to dry for 15 min in air. Filters were wetted in HBB buffer (25 mM HEPES-KOH, 25 mM NaCl, 5 mM MgCl$_2$, 1 mM DTT, pH 7.7), and blocked for 60 min in HBB with 5% non-fat dried milk and 0.05% NP-40, and for 30 min in HBB with 1% non-fat dried milk and 0.02% NP-40. They were next incubated overnight with labelled protein at 275,000 cpm/ml in Hyb buffer (20 mM HEPES-KOH, 50 mM KCL, 0.1 mM EDTA, 2.5 mM MgCl$_2$, 0.1 mM ATP, 1% non-fat dried milk, 0.02% NP-40, 1 mM DTT, pH 7.7), and washed three times for 7, 5, and 2 min, respectively, in Hyb buffer without labelled protein. All blocking, incubation, and washing steps were performed at 4° C. Filters were air dried and analyzed by exposing X-ray film, or by quantitatively imaging of radioactivity on an Ambis phosphorimager.

Membrane Localization of ZipA

For detergent solubilization of membrane proteins, an overnight culture of strain PB103 was diluted 200× in 1 liter of LB medium, and incubated until an OD$_{600}$. of 1.0 was reached. Cells were collected by centrifugation, washed once in cold saline, resuspended in 9.0 ml of cold cell breaking buffer (CBB conatins 20 mM Tris-Cl, 25 mM NaCl, 5 mM EDTA, 3.6 mM β-mercaptoethanol, pH 8.0), and broken by three passages through a French pressure cell followed by very brief sonication to reduce viscosity. The pressate was subjected to centrifugation at 200,000×g for 3 hrs at 8° C., the supernatant (S200) removed, and the pellet fraction (P200) resuspended in 2.0 ml of CBB. Aliquots (0.1 ml, 5.4 mg protein) of this were brought up to 0.5 ml of either CBB alone, or CBB with 6 M urea, 0.5% Triton-X100, or 0.2% Sarkosyl (final concentrations), and the mixtures were incubated at room temperature in a head over head mixer for 1 hr. Soluble material was separated from insoluble material by centrifugation (200,000×g for 1 hour at 4 C), the latter homogenized in 0.5 ml CBB by sonication (setting 2, approximately 20 seconds, on ice), and equal samples of each used for SDS-PAGE and affinity blotting.

To fractionate crude membrane preparations into the different membrane components, the procedure of Ishidate et al. was modified as follows. Briefly, cells from a logaritmically growing culture (500 ml LB) of strain PB103 were harvested at an OD$_{600}$ of 1.0 by centrifugation, washed with cold saline, and resuspended in 10 ml of 20% sucrose (All sucrose solutions were prepared w/w, in 10 mM Hepes-KOH, pH 7.4) and 10 µg/ml each of DNase and RNase. Cells were broken by three passages through a French pressure cell (10,000 psi) after which EDTA was added to 5 mM. To obtain a crude membrane preparation, 1.7 ml of the pressate was loaded on each of two gradients (SGO), which were prepared by layering 2.5 ml 25% sucrose on top of an 0.8 ml 60% sucrose cushion. The gradients were spun in an SW50.1 rotor at 37,000×g for 4 hr at 4° C. Crude membrane was recovered from the cushion by aid of a syringe, diluted with 10 mM HEPES-KOH (pH 7.4) to a refractive index of 1.3650 and a volume of 1.7 ml, and loaded on top of a sedimentation sucrose gradient (SG1) prepared by layering 60% (0.5 ml), 55% (1.0 ml), 50% (2.1 ml), 45% (2.1 ml), 40% (2.1 ml), 35% (1.5 ml), and 30% (1.0 ml) sucrose solutions. After centrifugation in an SW41 rotor at 39,000×g for 20 hrs at 4° C., fractions (0.33 ml) were collected from the bottom of the tube. The protein concentration and refractive index were determined for each fraction, and the latter was converted to the corresponding specific gravity value using ISCO tables (9th edition). Appropriate fractions were pooled and each pool was adjusted to a volume of 2.0 ml and a refractive index of 1.4285, by addition of 10 mM HEPES-KOH (pH 7.4) and powdered sucrose. From each pool, 0.2 ml was saved, and the rest was incorporated into a floatation sucrose gradient (SG2) which consisted, from bottom to top, of 67% (0.5 ml), pooled sample (1.8 ml), 50% (1.8 ml), 45% (3.0 ml), 40% (2.0 ml), 35% (1.0 ml), and 30% sucrose. After centrifugation in an SW41 rotor at 36,000×g for 72 hrs at 4° C., fractions (0.30 ml) were collected and analyzed as above, after which appropriate fractions were pooled. These pooled fractions, as well as the remainder of the pooled fractions from SG1, were adjusted to a sucrose concentration of less than 10% by addition of CBB to a volume of 10 ml. Membranes were colected by centrifugation in an SW50.1 rotor at 38,000×g for 2 hours at 4 C, and resuspended in 0.1 ml CBB. Aliquots were subsequently subjected to SDS-PAGE and affinity blotting as described above.

The results (not shown) can be summarized as follows. First, ZipA co-fractionated with the inner membrane fraction of cells during both sedimentation and floatation in sucrose gradients. This demonstrates that ZipA is truly associated with the inner membrane. Second, ZipA could be solubilized by detergent but not by urea. This indicates that ZipA is an integral membrane protein (i e., traverses the membrane).

Yeast Two-hybrid System

While the present invention allows for a cell-free screening assay, cellular screening assays are also contemplated. A Yeast two-hybrid system (commercially available from Clontech) allows for the detection of protein-protein interactions in yeast. See generally, Ausubel et al., *Current Protocols in Molecular Biology* (John Wileyt & Sons) (pp.13.14.1–13.14.14). The system can be used to screen specially constructed cDNA libraries for proteins that interact with a target protein (e.g., ZipA or FtsZ proteins or fragments thereof). The present invention contemplates the use of the two-hybrid system to screen for compounds that will bind to either the ZipA protein or FtsZ protein. Compounds (e.g., proteins) identified in a two-hybrid creen which bind to the FtsZ protein and which are not ZipA proteins may represent compounds capable of blocking the interaction of ZipA protein and FtsZ protein. Similarly, compounds which bind to the ZipA protein which are not FtsZ proteins may represent compounds capable of blocking the interaction of ZipA and FtsZ.

From the above, it should be clear that the present invention provides compounds and methods for screening large numbers of test compounds for antimicrobial activity. By using bacterial proteins in vitro to detect compounds, the present invention allows for a cell-free screening system.

We claim:

1. A purified protein having an amino acid sequence comprising SEQ ID NO:2.

2. The protein of claim 1, further comprising a label.

3. The protein of claim 1, wherein said label is a radiolabel.

4. A fusion protein comprising at least a portion of ZipA protein and a non-ZipA protein.

5. The fusion protein of claim 4, wherein said non-ZipA protein comprises green fluorescent protein from *Aequorea Victoria*.

6. A purified protein having an amino acid sequence comprising SEQ ID NO:2, wherein said protein is immobilized.

7. The protein of claim 6, wherein said protein is immobilized on nitrocellulose.

8. The protein of claim 6, wherein said protein is immobilized on a column.

9. The protein of claim 6, wherein said protein is immobilized on a bead.

10. The protein of claim 6, wherein said protein is immobilized in a microplate.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 2160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
CAATACCAGG GATGAAGTAA AGAATTAGTA ATACAATTGC GCGCGGCAGA TACCAGGCAA      60

ATTTTTGCCA TTCGCGTTTC ATGATTCGCG GCACATCTTT CATGATACCG AAAATCCCGG     120

TATCTGGCGG TGTAGCGCCA GTCAATCGTG CTTCCAGTTG TTCAGCCAAT AAACCGTTAA     180

ACGGAGCGGC AATCCAGTTA GCAATCGTGG AGAAGAAATA GCCAAACACT AACAGCACAG     240

AGATGACACG CAGAGGCCAC AACAGATAAC TCAGCCATTG TAGCCAGTCC GGAACGTAAC     300

TCATGAGAGT CGGGATCCAG ACATCGAGCT GTGTAAAGAG CCACCAGAAT GCGCCCCCCA     360

TCAACAAAAT ATTGACCAGC AGCGGTAAAA TAACGAAACG CCGAATCCCA GGTTGCGAGA     420

CGAGCTTCCA GCCTTGCGCA AAATAGTAAA AACCGCTGCG TGGGGCAGAT GTGAATGATG     480

AAACCATAAT CAGGATGAGC TCCTTTTGAC CAATCCCAGG AAAATTCTGC GTATTTTACC     540

GGGTAATTGC GCAATGGACA GTTAGGATAT GTTCGAAAAA ACAGCAAAAA GCACGATTTC     600

ATCTATCTTT GTGCTGTGAA AGTTAATAGT GCACTTGCAC TTGAGGTAAT CGGCAAATAC     660

TCTTAGTGAG TAAATGTTTG CCGTGGTGGC AAGGTGTTAG AACAACAGAG AATATAATGA     720

TGCAGGATTT GCGTCTGATA TTAATCATTG TTGGCGCGAT CGCCATAATC GCTTTACTGG     780

TACATGGTTT CTGGACCAGC CGTAAAGAAC GATCTTCTAT GTTCCGCGAT CGGCCATTAA     840

AACGAATGAA GTCAAAACGT GACGACGATT CTTATGACGA GGATGTCGAA GATGATGAGG     900

GCGTTGGTGA GGTTCGTGTT CACCGCGTGA ATCATGCCCC GGCTAACGCT CAGGAGCATG     960

AGGCTGCTCG TCCGTCGCCG CAACACCAGT ACCAACCGCC TTATGCGTCT GCGCAGCCGC    1020

GTCAACCGGT CCAGCAGCCG CCTGAAGCGC AGGTACCGCC GCAACATGCT CCGCATCCAG    1080

CGCAGCCGGT GCAGCAGCCT GCCTATCAGC CGCAGCCTGA ACAGCCGTTG CAGCAGCCAG    1140

TTTCGCCACA GGTCGCGCCA GCGCCGCAGC CTGTGCATTC AGCACCGCAA CCGGCACAAC    1200

AGGCTTTCCA GCCTGCAGAA CCCGTAGCGG CACCACAGCC TGAGCCTGTA GCGGAACCTG    1260

CTCCAGTTAT GGATAAACCG AAGCGCAAAG AAGCGGTGAT TATCATGAAC GTCGCGGCGC    1320

ATCACGGTAG CGAGCTAAAC GGTGAAGCTC TTCTTAACAG CATTCAACAA GCGGGCTTCA    1380

TTTTTGGCGA TATGAATATT TACCATCGTC ATCTTAGCCC GGATGGCAGC GGCCCGGCGT    1440

TATTCAGCCT GGCGAATATG GTGAAACCGG GAACCTTTGA TCCTGAAATG AAGGATTTCA    1500
```

```
CTACTCCGGG TGTCACTATC TTTATGCAGG TACCGTCTTA CGGTGACGAG CTGCAGAACT    1560

TCAAGCTGAT GCTGCAATCT GCGCAGCATA TTGCCGATGA AGTGGGCGGT GTCGTGCTTG    1620

ACGATCAGCG CCGTATGATG ACTCCGCAGA AATTGCGCGA GTACCAGGAC ATCATCCGCG    1680

AAGTCAAAGA CGCCAACGCC TGATACACTT AAGGCAAATT AACTCCTCTT CGAACCCCCG    1740

CTTGTCGGGG GTTTTTAGCA TTGATGGTGC GATATGGAAT CAATCGAACA ACAACTGACA    1800

GAACTGCGAA CGACGCTTCG CCATCATGAA TATCTTTATC ATGTGATGGA TGCGCCGGAA    1860

ATTCCCGACG CTGAATACGA CAGGCTGATG CGCGAACTGC GCGAGCTGGA AACCAAACAT    1920

CCAGAACTGA TTACGCCTGA TTCGCCTACT CAACGTGTAG GCGCTGCGCC GCTGGCGGCT    1980

TTCAGCCAGA TACGCCATGA AGTACCAATG CTGTCACTGG ATAACGTTTT TGATGAAGAA    2040

AGCTTTCTTG CTTTCAACAA ACGTGTGCAG GACCGTCTGA AAAACAACGA GAAAGTCACC    2100

TGGTGCTGTG AGCTGAAGCT GGATGGTCTT GCCGTCAGTA TTCTGTATGA AAATGGCGTT    2160
```

(2) INFORMATION FOR SEQ ID NO:2:

(i) SEQUENCE CHARACTERISTICS:
        (A) LENGTH: 328 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:2:

```
Met Met Gln Asp Leu Arg Leu Ile Leu Ile Ile Val Gly Ala Ile Ala
1               5                   10                  15

Ile Ile Ala Leu Leu Val His Gly Phe Trp Thr Ser Arg Lys Glu Arg
                20                  25                  30

Ser Ser Met Phe Arg Asp Arg Pro Leu Lys Arg Met Lys Ser Lys Arg
            35                  40                  45

Asp Asp Asp Ser Tyr Asp Glu Asp Val Glu Asp Glu Gly Val Gly
        50                  55                  60

Glu Val Arg Val His Arg Val Asn His Ala Pro Ala Asn Ala Gln Glu
65                  70                  75                  80

His Glu Ala Ala Arg Pro Ser Pro Gln His Gln Tyr Gln Pro Pro Tyr
                85                  90                  95

Ala Ser Ala Gln Pro Arg Gln Pro Val Gln Gln Pro Pro Glu Ala Gln
            100                 105                 110

Val Pro Pro Gln His Ala Pro His Pro Ala Gln Pro Val Gln Gln Pro
        115                 120                 125

Ala Tyr Gln Pro Gln Pro Glu Gln Pro Leu Gln Pro Val Ser Pro
    130                 135                 140

Gln Val Ala Pro Ala Pro Gln Pro Val His Ser Ala Pro Gln Pro Ala
145                 150                 155                 160

Gln Gln Ala Phe Gln Pro Ala Glu Pro Val Ala Ala Pro Gln Pro Glu
                165                 170                 175

Pro Val Ala Glu Pro Ala Pro Val Met Asp Lys Pro Lys Arg Lys Glu
            180                 185                 190

Ala Val Ile Ile Met Asn Val Ala Ala His His Gly Ser Glu Leu Asn
        195                 200                 205

Gly Glu Ala Leu Leu Asn Ser Ile Gln Gln Ala Gly Phe Ile Phe Gly
    210                 215                 220

Asp Met Asn Ile Tyr His Arg His Leu Ser Pro Asp Gly Ser Gly Pro
225                 230                 235                 240
```

```
Ala Leu Phe Ser Leu Ala Asn Met Val Lys Pro Gly Thr Phe Asp Pro
                245                 250                 255

Glu Met Lys Asp Phe Thr Thr Pro Gly Val Thr Ile Phe Met Gln Val
            260                 265                 270

Pro Ser Tyr Gly Asp Glu Leu Gln Asn Phe Lys Leu Met Leu Gln Ser
            275                 280                 285

Ala Gln His Ile Ala Asp Glu Val Gly Val Val Leu Asp Asp Gln
        290                 295                 300

Arg Arg Met Met Thr Pro Gln Lys Leu Arg Glu Tyr Gln Asp Ile Ile
305                 310                 315                 320

Arg Glu Val Lys Asp Ala Asn Ala
                325
```

(2) INFORMATION FOR SEQ ID NO:3:

(i) SEQUENCE CHARACTERISTICS:
       (A) LENGTH: 327 amino acids
       (B) TYPE: amino acid
       (C) STRANDEDNESS: Not Relevant
       (D) TOPOLOGY: Not Relevant (ii) MOLECULE TYPE: protein (xi) SEQUENCE DESCRIPTION: SEQ ID NO:3:

```
Asp Leu Asn Thr Ile Leu Ile Val Gly Ile Val Ala Leu Val Ala
1               5                   10                  15

Leu Ile Val His Gly Leu Trp Ser Asn Arg Arg Glu Lys Ser Lys Tyr
            20                  25                  30

Phe Asp Lys Ala Asn Lys Phe Asp Arg Thr Ser Leu Thr Ser Arg Ser
            35                  40                  45

His Thr Gln Glu Glu Met Val Gln Pro Asn Asn Ile Ser Pro Asn Thr
        50                  55                  60

Tyr Val Glu Asn Gly His Thr Pro Ile Pro Gln Pro Thr Thr Glu Lys
65                  70                  75                  80

Leu Pro Ser Glu Ala Glu Leu Ile Asp Tyr Arg Gln Ser Asp Lys Ser
                85                  90                  95

Val Asp Asp Ile Lys Ile Ser Ile Pro Asn Thr Gln Pro Ile Tyr Asp
            100                 105                 110

Met Gly Asn His Arg Ser Glu Pro Ile Gln Pro Thr Gln Pro Gln Tyr
            115                 120                 125

Asp Met Pro Thr Ala Asn Asn Val Ala Ser Met Thr Leu Glu Gln Leu
        130                 135                 140

Glu Ala Gln Ser Gln Asn Val Gly Phe Asn Gly Ile Asn Ser Ser Ser
145                 150                 155                 160

Pro Glu Leu Arg Val Gln Leu Ala Glu Leu Ser His Glu Glu His Gln
                165                 170                 175

Val Asp Tyr Asn Leu Ser Phe Asn Glu Pro Lys Ala Glu Thr Thr Ala
            180                 185                 190

His Pro Lys Gln Thr Thr Gly Tyr Ile Gln Leu Tyr Leu Ile Pro Lys
            195                 200                 205

Ser Ser Glu Glu Phe Asn Gly Ala Lys Leu Val Gln Ala Leu Glu Asn
        210                 215                 220

Leu Gly Phe Ile Leu Gly Lys Asp Glu Met Tyr His Arg His Leu Asp
225                 230                 235                 240

Leu Ser Val Ala Ser Pro Val Leu Phe Ser Val Ala Asn Leu Glu Gln
                245                 250                 255
```

```
Pro Gly Thr Phe Asn Ala Tyr Asn Leu Ala Glu Phe Asn Thr Ile Gly
            260                 265                 270

Ile Val Leu Phe Met Gln Leu Pro Ser Pro Gly Asn Asn Leu Ala Asn
            275                 280                 285

Leu Arg Met Met Met Arg Ala Ala His Thr Leu Ala Glu Asp Leu Gln
            290                 295                 300

Gly Val Ile Leu Thr Glu Gln Glu Ile Phe Asp Ala Asn Ala Glu
305                 310                 315                 320

Gln Ala Tyr Leu Ala Arg Val
                325
```

(2) INFORMATION FOR SEQ ID NO:4:

(i) SEQUENCE CHARACTERISTICS:
  (A) LENGTH: 6 amino acids
  (B) TYPE: amino acid
  (C) STRANDEDNESS: Not Relevant
  (D) TOPOLOGY: Not Relevant (ii) MOLECULE TYPE: peptide (xi) SEQUENCE DESCRIPTION: SEQ ID NO:4:

```
Ile Leu Ile Ile Val Gly
1               5
```

(2) INFORMATION FOR SEQ ID NO:5:

(i) SEQUENCE CHARACTERISTICS:
  (A) LENGTH: 10 amino acids
  (B) TYPE: amino acid
  (C) STRANDEDNESS: Not Relevant
  (D) TOPOLOGY: Not Relevant (ii) MOLECULE TYPE: peptide (ix) FEATURE:
  (A) NAME/KEY: Modified-site
  (B) LOCATION: 3
  (D) OTHER INFORMATION: /note= "The peptide at this
   location can be either Arg or Asn."

(ix) FEATURE:
  (A) NAME/KEY: Modified-site
  (B) LOCATION: 4
  (D) OTHER INFORMATION: /note= "The peptide at this
   location can be either Leu or Thr."

(xi) SEQUENCE DESCRIPTION: SEQ ID NO:5:

```
Asp Leu Xaa Xaa Ile Leu Ile Ile Val Gly
1               5                   10
```

(2) INFORMATION FOR SEQ ID NO:6:

(i) SEQUENCE CHARACTERISTICS:
  (A) LENGTH: 13 amino acids
  (B) TYPE: amino acid
  (C) STRANDEDNESS: Not Relevant
  (D) TOPOLOGY: Not Relevant (ii) MOLECULE TYPE: peptide (ix) FEATURE:
  (A) NAME/KEY: Modified-site
  (B) LOCATION: 7
  (D) OTHER INFORMATION: /note= "The peptide at this
   location can be either"

(ix) FEATURE:
  (A) NAME/KEY: Modified-site
  (B) LOCATION: 8
  (D) OTHER INFORMATION: /note= "The peptide at this location can be either Ile or Val."

(ix) FEATURE:
           (A) NAME/KEY: Modified-site
           (B) LOCATION: 10
           (D) OTHER INFORMATION: /note= "The peptide at this
               locaiton can be either Ile or Leu."

(ix) FEATURE:
           (A) NAME/KEY: Modified-site
           (B) LOCATION: 11
           (D) OTHER INFORMATION: /note= "The peptide at this
               location can be either Ile or Val."

(xi) SEQUENCE DESCRIPTION: SEQ ID NO:6:

Ile Leu Ile Ile Val Gly Xaa Xaa Ala Xaa Xaa Ala Leu
1               5                   10

(2) INFORMATION FOR SEQ ID NO:7:

(i) SEQUENCE CHARACTERISTICS:
           (A) LENGTH: 17 amino acids
           (B) TYPE: amino acid
           (C) STRANDEDNESS: Not Relevant
           (D) TOPOLOGY: Not Relevant (ii) MOLECULE TYPE: peptide (ix) FEATURE:
           (A) NAME/KEY: Modified-site
           (B) LOCATION: 7
           (D) OTHER INFORMATION: /note= "The peptide at this
               location can be either Ala or Leu."

(ix) FEATURE:
           (A) NAME/KEY: Modified-site
           (B) LOCATION: 8
           (D) OTHER INFORMATION: /note= "The peptide at this
               location can be either Ile or Val."

(ix) FEATURE:
           (A) NAME/KEY: Modified-site
           (B) LOCATION: 10
           (D) OTHER INFORMATION: /note= "The peptide at this
               location can be either Ile or Leu."

(ix) FEATURE:
           (A) NAME/KEY: Modified-site
           (B) LOCATION: 11
           (D) OTHER INFORMATION: /note= "The peptide at this
               location can be either Ile or Val."

(ix) FEATURE:
           (A) NAME/KEY: Modified-site
           (B) LOCATION: 14
           (D) OTHER INFORMATION: /note= "The peptide at this
               location can be either Ile or Leu."

(xi) SEQUENCE DESCRIPTION: SEQ ID NO:7:

Ile Leu Ile Ile Val Gly Xaa Xaa Ala Xaa Xaa Ala Leu Xaa Val His
1               5                   10                  15

Gly (2) INFORMATION FOR SEQ ID NO:8:

(i) SEQUENCE CHARACTERISTICS:
           (A) LENGTH: 6 amino acids
           (B) TYPE: amino acid
           (C) STRANDEDNESS: Not Relevant
           (D) TOPOLOGY: Not Relevant (ii) MOLECULE TYPE: peptide (ix) FEATURE:
           (A) NAME/KEY: Modified-site (B) LOCATION: 3
          (D) OTHER INFORMATION: /note= "The peptide at this
              location can be either Ile or Leu."

(xi) SEQUENCE DESCRIPTION: SEQ ID NO:8:

Ala Leu Xaa Val His Gly
1               5

(2) INFORMATION FOR SEQ ID NO:9:

(i) SEQUENCE CHARACTERISTICS:
          (A) LENGTH: 8 amino acids
          (B) TYPE: amino acid
          (C) STRANDEDNESS: Not Relevant
          (D) TOPOLOGY: Not Relevant (ii) MOLECULE TYPE: peptide (ix) FEATURE:
          (A) NAME/KEY: Modified-site
          (B) LOCATION: 3
          (D) OTHER INFORMATION: /note= "The peptide at this
              location can be either Ile or Leu."

(ix) FEATURE:
          (A) NAME/KEY: Modified-site
          (B) LOCATION: 7
          (D) OTHER INFORMATION: /note= "The peptide at this
              location can be either Phe or Leu."

(xi) SEQUENCE DESCRIPTION: SEQ ID NO:9:

Ala Leu Xaa Val His Gly Xaa Trp
1               5

(2) INFORMATION FOR SEQ ID NO:10:

(i) SEQUENCE CHARACTERISTICS:
          (A) LENGTH: 5 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO:10:

Tyr His Arg His Leu
1               5

(2) INFORMATION FOR SEQ ID NO:11:

(i) SEQUENCE CHARACTERISTICS:
          (A) LENGTH: 8 amino acids
          (B) TYPE: amino acid
          (C) STRANDEDNESS: Not Relevant
          (D) TOPOLOGY: Not Relevant (ii) MOLECULE TYPE: peptide (ix) FEATURE:
          (A) NAME/KEY: Modified-site
          (B) LOCATION: 2
          (D) OTHER INFORMATION: /note= "The peptide at this
              location can be either Ala or Val."

(ix) FEATURE:
          (A) NAME/KEY: Modified-site
          (B) LOCATION: 6
          (D) OTHER INFORMATION: /note= "The peptide at this
              location can be either Leu or Val."

(xi) SEQUENCE DESCRIPTION: SEQ ID NO:11:

Pro Xaa Leu Phe Ser Xaa Ala Asn
1               5

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:12:

Pro Gly Thr Phe
1

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Modified-site
        (B) LOCATION: 1
        (D) OTHER INFORMATION: /note= "The peptide at this
            location can be either Ile or Leu."

(xi) SEQUENCE DESCRIPTION: SEQ ID NO:13:

Xaa Phe Met Gln
1

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Modified-site
        (B) LOCATION: 1
        (D) OTHER INFORMATION: /note= "The peptide at this
            location can be either Ile or Leu."

(ix) FEATURE:
        (A) NAME/KEY: Modified-site
        (B) LOCATION: 5
        (D) OTHER INFORMATION: /note= "The peptide at this
            location can be either Val or Leu."

(xi) SEQUENCE DESCRIPTION: SEQ ID NO:14:

Xaa Phe Met Gln Xaa Pro Ser
1                 5

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
ACAGAGATCC ATATGATGCA GGATTTGCGT CTG                              33

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TTAACCAAGC TTAAGTGTAT CAGGCGTTGG                                  30

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

AAGTCTCGAG GGCGTTGGCG TCTTTGAC                                    28

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:18:

Leu Glu Asp Pro Pro Ala Glu Phe
1               5

(2) INFORMATION FOR SEQ ID NO:19:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:19:

Met Gly His His His His His His His His His Ser Ser Gly His
1               5                   10                  15

Ile Glu Gly Arg His Met Asp Tyr Lys Asp Asp Asp Lys Ala Arg
                20                  25                  30

Arg Ala Ser Val Glu Phe His Met Ala Ser Met Thr Gly Gly Gln Gln
                35                  40                  45

Met Gly Arg Gly Ser
50

(2) INFORMATION FOR SEQ ID NO:20:

(i) SEQUENCE CHARACTERISTICS:
        (A) LENGTH: 14 amino acids
        (B) TYPE: amino acid
        (C) STRANDEDNESS: Not Relevant
```

(D) TOPOLOGY: Not Relevant (ii) MOLECULE TYPE: peptide (xi) SEQUENCE DESCRIPTION: SEQ ID NO:20:

Met Ala Ser Met Thr Gly Gly Gln Gln Met Gly Arg Gly Ser
1               5                   10

(2) INFORMATION FOR SEQ ID NO:21:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:21:

Met Gly His His His His His His His His His Ser Ser Gly His
1               5                   10                  15

Ile Glu Gly Arg His
            20

(2) INFORMATION FOR SEQ ID NO:22:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:22:

Met Asp Tyr Lys Asp Asp Asp Lys Ala Arg Arg Ala Ser Val Glu
1               5                   10                  15

Phe (2) INFORMATION FOR SEQ ID NO:23:

(i) SEQUENCE CHARACTERISTICS:
        (A) LENGTH: 54 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:23:

Met Gly His His His His His His His His His Ser Ser Gly His
1               5                   10                  15

Ile Glu Gly Arg His Met Asp Tyr Lys Asp Asp Asp Lys Ala Arg
            20                  25                  30

Arg Ala Ser Val Glu Phe His Met Ala Ser Met Thr Gly Gln Gln
            35                  40                  45

Met Gly Arg Gly Ser His
            50

(2) INFORMATION FOR SEQ ID NO:24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GGAGGATCCC ATATGTTTGA ACCAATGGAA C                    31

(2) INFORMATION FOR SEQ ID NO:25:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TTCCGGTCGA CTCTTAATCA GCTTGCTTAC G                    31